(12) United States Patent
Guertin et al.

(10) Patent No.: US 10,765,551 B1
(45) Date of Patent: *Sep. 8, 2020

(54) METHOD AND SYSTEM FOR PROVIDING WHOLE BODY CRYOTHERAPY

(71) Applicant: IMPACT CRYOTHERAPY, INC., Atlanta, GA (US)

(72) Inventors: Eugene L. Guertin, Atlanta, GA (US); Thomas S. Sanders, Atlanta, GA (US)

(73) Assignee: IMPACT CRYOTHERAPY, INC., Atlanta, GA (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/376,568

(22) Filed: Dec. 12, 2016

Related U.S. Application Data

(60) Provisional application No. 62/407,405, filed on Oct. 12, 2016, provisional application No. 62/415,262, filed on Oct. 31, 2016.

(51) Int. Cl.
*A61F 7/00* (2006.01)

(52) U.S. Cl.
CPC .... *A61F 7/0053* (2013.01); *A61F 2007/0064* (2013.01); *A61F 2007/0093* (2013.01); *A61F 2007/0094* (2013.01); *A61F 2007/0095* (2013.01)

(58) Field of Classification Search
CPC ....... A61F 7/0053; A61F 7/00; A61F 2007/00
USPC ...................................... 607/83–87
See application file for complete search history.

(56) References Cited

U.S. PATENT DOCUMENTS

| | | | |
|---|---|---|---|
| 2,817,340 A | 12/1957 | Cuvier | |
| 4,784,140 A * | 11/1988 | Donnerback | A61F 7/0053 128/DIG. 27 |
| 4,880,003 A | 11/1989 | Donnerhack et al. | |
| 8,162,930 B2 | 4/2012 | Brojek et al. | |
| 8,316,652 B2 | 11/2012 | Decourcelle et al. | |
| 2005/0096714 A1 * | 5/2005 | Freedman, Jr. | A61F 7/00 607/104 |
| 2013/0025302 A1 * | 1/2013 | Lyubchenko | A61F 7/0053 62/89 |
| 2014/0257440 A1 * | 9/2014 | Muehlbauer | A61F 7/00 607/99 |
| 2015/0094702 A1 | 4/2015 | Shuppo | |
| 2015/0285389 A1 * | 10/2015 | Mulder | F16K 17/003 137/12 |
| 2016/0089262 A1 | 3/2016 | Kuehne | |

* cited by examiner

*Primary Examiner* — Lynsey C Eiseman
(74) *Attorney, Agent, or Firm* — Smith Tempel; Steven P. Wigmore

(57) ABSTRACT

A system and method for automatically producing and monitoring a cryotherapy session within a chamber includes a plumbing system coupled to the chamber for cooling the chamber. A central controller may be coupled to the plumbing system. The central controller may be operable for: initiating the cryotherapy session within the chamber with a cryogenic gas flowing through the plumbing system for cooling the chamber to a first temperature; determining if the first temperature has been reached within the chamber; determining if a check-in command has been received for the cryotherapy session; and stopping the cryotherapy session after a predetermined period of time. The central controller may also monitor a cooling rate for the chamber and a heater associated with the cooling rate.

16 Claims, 25 Drawing Sheets

METHOD AND SYSTEM FOR PROVIDING WHOLE BODY CRYOTHERAPY

DESCRIPTION OF THE RELATED ART

Conventional Whole Body Cryotherapy (WBC) systems/machines for exposing subjects to very cold air temperatures, such as on the order between about minus (−) 312.0 degrees F. to about minus (−)302.0 degrees F., have been manufactured for some time. However, conventional WBC systems have suffered from many drawbacks.

One drawback of conventional WBC systems is that many systems have been constructed on a very large in scale. For example, some systems enclose entire stairwells and/or large rectangular chambers or small rooms and require both the stairwells and the small rooms to be cooled. Such chambers/small rooms could house several people, similar to conventional sauna rooms. Such systems having this much volume/space to cool to reach temperatures as described above require a significant amount of energy and cooling gases to reach desired cool temperatures that are constant throughout the space/volume.

Further, given the size of such systems, the amount of materials to construct a single system (i.e. the materials for the stairs, the materials to enclose the stairs, the materials for the rooms, etc.) may be very significant. Such large systems are not movable and usually must be made a permanent fixture within a structure like a building.

Often, conventional systems do not provide for consistent, repeatable cooling/cryotherapy sessions where sessions may last on the order of minutes and intervals between sessions may also last on the order of minutes. Some conventional systems require significant down time in between cooling sessions, such as on the order of ten to fifteen minutes between sessions. Such ten to fifteen minute downtime intervals may be significant when a system is designed to provide sessions for numerous people over the course of a single business day.

Another problem of a conventional systems is the lack of precise control of their operation. While a timer alone may help in the safe operation of a cryotherapy system, a timer alone often cannot offer additional safeguards to prevent improper and/or deliberate mis-operation of the cryotherapy system.

Accordingly, what is needed in the art is an intelligent cryotherapy system which may facilitate the safe operation of the system while also improving the cooling efficiency of the system. Another need in the art is for a cryotherapy system which provides a volume that is sufficient to envelope/enclose a single person while offering very precise control over the temperature within that volume.

SUMMARY OF THE DISCLOSURE

A method and system for providing whole body cryotherapy sessions may include a cabin comprising a structural aluminum frame that may have removable covered insulated panels. The system may further include a stainless steel and copper liquid nitrogen to nitrogen gas delivery system that is under control of a an electronic controller. The electronic controller may comprise hardware and/or software. In one exemplary embodiment, the electronic controller may comprise a Programmable Logic Controller (PLC) that may have a custom user interface which may be displayed on a display device, such as a liquid crystal display (LCD). The electronic controller may provide for some unique safety features that may include unique screen displays and requested user input via the screen displays when the system is operated during cryotherapy sessions. The system may also include simple mechanical machines in the form of risers/steps for adjusting for the height of different human subjects.

A method for automatically producing and monitoring a cryotherapy session within a chamber may include receiving input for a first temperature for the chamber associated with the cryotherapy session within the chamber. Next, a pre-cooling session for cooling the chamber to a second temperature which is different than the first temperature may be started. Next, it is determined if the second temperature has been reached in the chamber.

If the second temperature is reached, then the cryotherapy session is initiated within the chamber with a cryogenic gas for cooling the chamber to the first temperature. During the cryotherapy session, it may be determined if the first temperature has been reached within the chamber as well as whether a stop command has been received for the cryotherapy session. Further, during the cryotherapy session, it may be determined if a check-in command has been received for the cryotherapy session. The check-in and stop commands may comprise safety features/functions for the cryotherapy session.

Also, during a cryotherapy session, it may be determined if an overheat condition exists for a heater and/or if the heater malfunctions due to an electrical short or other condition and/or if a cooling rate for the chamber is being met. It may also be determined if the pressure of the conduits supplying the cooling fluid or cooling gas, such as, but not limited to, liquid nitrogen is within a "normal range."

The input for the first temperature may be received through a touch-screen display device mounted on a side wall of the chamber. During a cryotherapy session, it may be determined if a predetermined time limit associated with the cryotherapy session has expired.

A system for automatically producing and monitoring a cryotherapy session within a chamber may include a chamber defining a closed volume. The system may also include a plumbing system coupled to the chamber for cooling the chamber. A central controller may be coupled to the plumbing system.

The central controller may be operable for: initiating the cryotherapy session within the chamber with a cryogenic gas flowing through the plumbing system for cooling the chamber to a first temperature; determining if the first temperature has been reached within the chamber; determining if a check-in command has been received for the cryotherapy session; and stopping the cryotherapy session after a predetermined period of time.

The central controller may be operable for initiating a pre-cooling session for cooling the chamber to a second temperature which is different than the first temperature; and determining if the second temperature has been reached in the chamber. The system may also include a riser that is positioned within the volume of the chamber for supporting a subject that is exposed to the cryotherapy session.

The system may include a first nozzle having a plurality of jets for cooling the chamber during the cryotherapy session. The system may also have a second nozzle that cools the chamber for the pre-cooling stage.

This summary is provided to introduce a selection of concepts that are further described below in the detailed description. This summary is not intended to identify key or essential features of the claimed subject matter, nor is it intended to be used as an aid in limiting the scope of the claimed subject matter

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures.

DETAILED DESCRIPTION

Figure 1A:
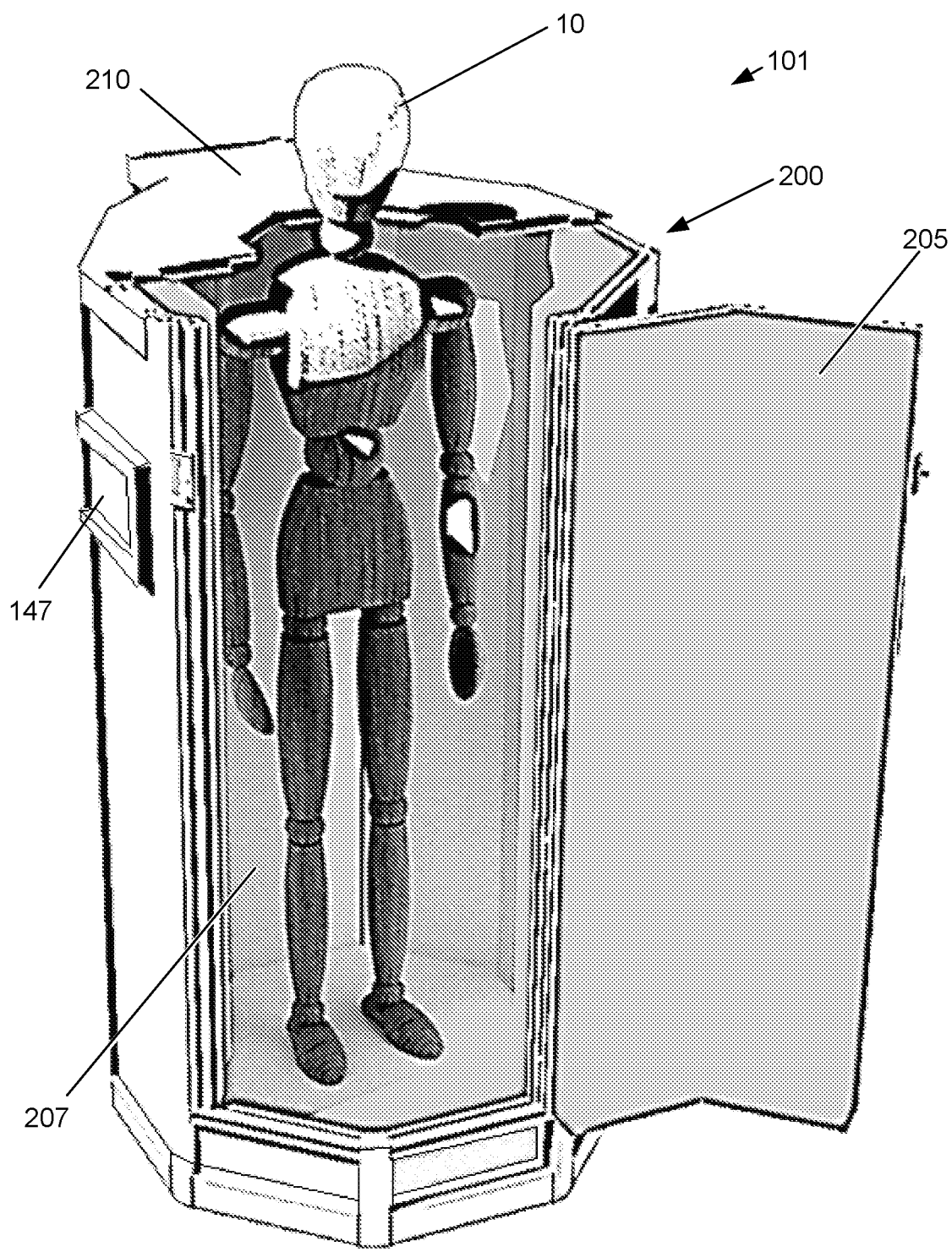
FIG. 1A illustrates one exemplary embodiment of a cryogenic chamber used in a system for providing whole body cryotherapy.

The word "exemplary" is used herein to mean "serving as an example, instance, or illustration." Any aspect described herein as "exemplary" is not necessarily to be construed as exclusive, preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

As used in this description, the terms "component," "database," "module," "system," "thermal energy generating component," "processing component," "multimedia processing component" and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component.

In this description, the terms "central processing unit ("CPU")," "digital signal processor ("DSP")," "graphical processing unit ("GPU")," and "chip" are used interchangeably. Moreover, a CPU, DSP, GPU or a chip may be comprised of one or more distinct processing components generally referred to herein as "core(s)."

In this description, it will be understood that the terms "thermal" and "thermal energy" may be used in association with a device or component capable of generating or dissipating energy that can be measured in units of "temperature." Consequently, it will further be understood that the term "temperature," with reference to some standard value, envisions any measurement that may be indicative of the relative warmth, or absence of heat, of a "thermal energy" generating device or component. For example, the "temperature" of two components is the same when the two components are in "thermal" equilibrium.

A whole body Cryotherapy (WBC) system and method are described. The system may include a structure defining a volume of space that is capable of enclosing a human body except for a head of the human body. The system may also have a gas delivery system coupled to the structure for delivering gas into the structure that cools the volume of space and a first temperature sensor coupled to the gas delivery system for measuring a temperature of the gas entering the volume of space. The system may also have a second temperature sensor coupled to the structure at a predetermined distance relative to a height of the structure for measuring a temperature of the volume of space; and an electronic controller coupled to the gas delivery system and the first and second temperature sensors.

The controller may maintain a temperature of the volume of space within a predetermined range for a predetermined length of time during a cryotherapy session. The controller may also conduct a pre-cooling operation prior to each cryotherapy session in order to remove excess heat within the volume of space. Each temperature sensor may comprise a resistance temperature detector.

The first temperature sensor may be positioned adjacent to a spray head which is part of the gas delivery system. The second temperature sensor is positioned at a height of about 24.0 inches relative to below a roof/top of the structure.

The controller may comprise a programmable logic controller. The controller during the cryotherapy session may maintain the volume of space at a temperature between about −312.0 degrees F. to about −302.0 degrees F. The predetermined length of time for cryotherapy session is between about 30.0 seconds to about 240.0 seconds; and more preferably, between about 60.0 seconds to about 210.0 seconds. And most preferable, the session has duration of about 180.0 seconds.

The controller lowers a temperature of the volume of space between about −20.0 degrees F. to about 20.0 degrees F. prior to initiating a cryotherapy session. And preferably, a desired pre-cool temperature of about −10.0 degrees F. is reached prior to a session.

For a given cryotherapy session of approximately (and usually not more than) three (3.0) minutes, the volume of the cryogenic fluid, such as liquid nitrogen, that is used is approximately 6.0 liters. The conversion of the liquid cryogenic fluid into gas takes place in the plumbing system and the volume of gas that is generated during the approximately three (3.0) minute session is approximately 148.0 cubic feet of gas. The temperature of the cryotherapy session during use usually comprises a range of between about −10.0 degrees C. to about −130.0 degrees C. Other ranges are possible and are included within the scope of this disclosure.

Referring now to FIG. 1A, this figure illustrates one exemplary embodiment of a cryogenic chamber 200 used in a system 101 for providing whole body cryotherapy. Some of the mechanical elements of the cryogenic chamber 200 may include a removable cover 210 and a movable door 205. These and other mechanical elements will be described in further detail below.

The removable cover 210 is designed to surround/envelope the head of a human subject 10. Another half of removable cover 210 (not illustrated in FIG. 1A, but see FIG. 7) may fold over such that the removable cover 210 completely surrounds the head of a human subject 10 in order to keep the cooling gases within the internal volume 207 defined by the cryogenic chamber 200.

Only a portion, specifically, one-half of the removable cover 210 is illustrated in FIG. 1A. Meanwhile, a functioning movable door 210 is designed to be both an exit and entrance to the internal volume 207 defined by chamber 200. The human subject 10 may open the movable door 205 to gain entrance into the internal volume 207 prior to a cryotherapy session. The human subject 10 may open the movable door to exit the internal volume 207 after a cryotherapy session.

Outside of the cryogenic chamber 200 there may be placed/positioned a display device 147. The display device 147 may provide status as well as control of cryotherapy sessions which may be provided within the volume 207 defined by the cryogenic chamber 200. The display device 147 may be coupled to a central controller 100 (not illustrated in FIG. 1A but see FIG. 1D) that is described in further detail below.

The cryogenic chamber 200 is usually cooled with liquid Nitrogen to generally between a temperature of about −10.0 to-about 130.0 degrees Celsius. The human subject 10 may wear thermal Socks, gloves, boots and will keep his or her head out of the cryogenic chamber 200 as illustrated in FIG. 1. The system 101 is designed to provide an optimal user experience for a short duration (i.e. usually no more than about three minutes).

Liquid Nitrogen (LN2) is one cryogenic fluid that may be used by the system 101 to achieve the temperatures noted above for cryotherapy sessions. The LN2 is typically converted to nitrogen gas as it enters the internal volume 207 defined by the chamber 200. When LN2 is converted to nitrogen gas, it can go through two key temperature transitions as understood by one of ordinary skill in the art: one first key temperature is the Triple Point (Boiling point) and the second key temperature is the Critical Temp. When LN2 is warmed to about −320.0 degrees F., it reaches its boiling point and begins its transition into a gas. By adding pressure during this stage the second key temperature comes into play and that is the critical point.

By supplying the LN2 from a cryogenic fluid supply 125 (See FIG. 1D) at about 22.0 to about 23.0 psi, it optimizes the temperature of the nitrogen gas during its phase change from liquid to gas at temperatures between about −312.0 F to about −302.0 F and thus avoids a saturation zone where liquid and gas LN2 may coexist.

When analyzing the thermodynamic effects of nitrogen gas once it is released into the chamber 200, it can best be explained by analyzing the enthalpy change from about −320.0-degrees F. to about −10.0 degrees F. Enthalpy in this case is defined as the transfer of heat due to the expansion of the nitrogen gas within the chamber 200 at a constant pressure of about 1.0 atm or about 14.4 psi.

LN2 @ about −320.0 has about −3372.0 j/mole of Enthalpy;

N2 @ about −320.0 has about 2178.0 j/mole of Enthalpy;
N2 @ about −10.0 F has about 6900.0 j/mole of Enthalpy;

The enthalpy increase from the boiling point of LN2 (about −320 F), to the Enthalpy of nitrogen gas at about −10.0 F equates to over about a 300.0% increase in Enthalpy from nitrogen's liquid state to nitrogen's gas state at −10.0 degrees F. Simply stated: there is a very large amount of heat being transferred due to the rapid expansion of the nitrogen gas. Nitrogen is usually heavier than air and as the nitrogen gas expands and continues to warm, it will tend to create temperature gradients within internal volume 207 defined by the chamber 200.

The system 101 uses two Resistance Temperature Detectors (RTDs) 105B in the chamber 200 (See FIG. 1D) to measure and control both the delivery temperature of the cryogenic gas and the temperature of internal volume 207 of the chamber 200 resulting from the delivery of the cryogenic gas into the chamber 200. Properly measuring the delivery temperature at the entry point into the chamber 200 may allow the system 101 to produce cryogenic gas (i.e. nitrogen gas) just warmer than the liquid gas phase change. This delivery method translates into to the most efficient use of the cryogenic fluid, which is usually LN2.

The entry temperatures into the chamber 200 ranges from about −312.0 to about −302.0 F. The system 101, and specifically the central controller 100 (See FIG. 1D) measures temperatures from at least two (2) locations within the chamber 200. A first temperature reading may occur at a first nozzle 802 (See also FIG. 14) for delivering the nitrogen gas into the chamber 200 insures that the gas entering the chamber 200 is regulated between about −312.0 F and −302.0 F.

The second temperature reading (See also FIG. 14) is usually measured at about 24.0 inches below the closable cover 210: this temperature reading may represent the average cabin temperature. Depending on the desired intensity of the WBC session the cabin temperatures can range between about −130.0 F to about −250.0 F. Alternate ranges include, but are not limited, to about 14.0 F to about −202.0 F.

The placement of each RTD 105 is important and it has been determined through various techniques by the inventors where the RTD placement is required. Through R&D and testing, one optimum location is selected to represent what the average temperature within volume 207 defined by chamber 200 may be at a given point in time. The RTD 105 may be placed at about 24.0 inches below the removable cover 210 of the chamber 200 usually provides an accurate representation of an average temperature internal volume 207 defined by the chamber 200.

In order to minimize temperature gradients that may occur within the chamber 200, the system 101 is designed with flow technology that continually mixes the cryogenic gas within the chamber 200 from the top of the chamber 200 to the bottom of the chamber 200. This flow mixing technology may help insure that a consistent temperature is maintained throughout the internal volume 207 defined by the chamber 200.

The system 101 also supports a unique feature/function which may be characterized as a "Pre-Cool" stage. The Pre-Cool stage addresses the ambient temperature of the chamber 200 before the cryogenic gas (i.e. nitrogen gas) is introduced into the chamber 200. With the Pre-Cool stage, the initial ambient temperature of the internal volume 207 is usually lowered. Before the air within the chamber 200 may be brought down to the desired temperature, a heat transfer will need to take place by having the cryogenic gas (i.e. nitrogen gas) remove heat from the internal volume 207. The desired pre-cool stage temperature is usually about −14.0 degrees F.

To achieve this desired pre-cool temperature/pre-cool stage is a function of time and ambient temperature and can also be affected by the amount of humidity in the internal volume 207: Less humidity usually translates to a faster pre-cool operation and more efficient use of the cryogenic gas. Conversely, if the system 101 is being operated with only a few minutes between WBC sessions, then the removal of heat is much less which equates to a short pre-cool operation which may also increase the overall efficiency of the system 101.

Figure 1B:
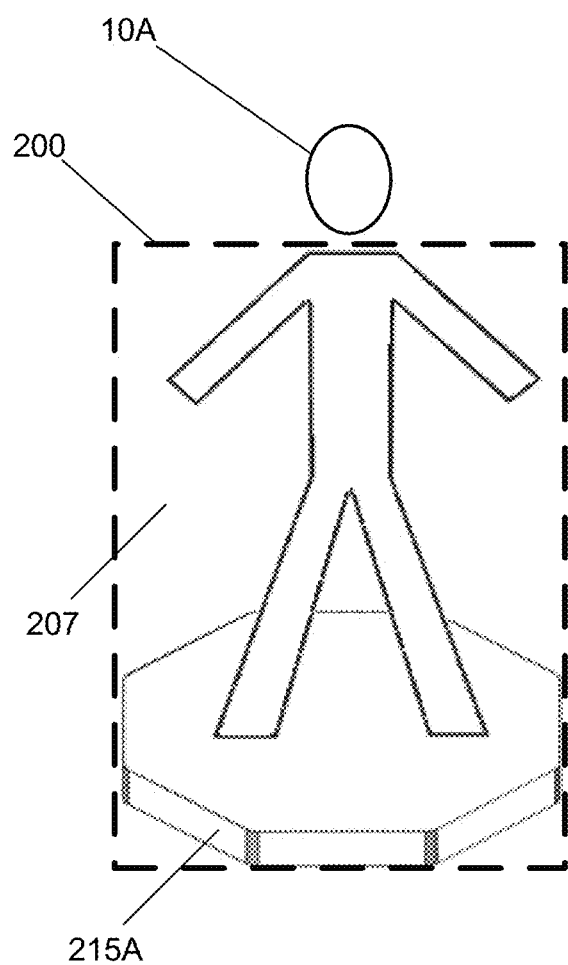
FIG. 1B illustrates one exemplary embodiment of a single riser used to support a human subject within a cryogenic chamber of a whole body cryotherapy system.

Referring now to FIG. 1B, this figure illustrates one exemplary embodiment of a single riser 215A used to support a human subject 10A within a cryogenic chamber 200 of a whole body cryotherapy system 101. Each riser 215 may have a predetermined thickness such that the height or size of the internal volume 207 may be adjusted to fit for various body types and sizes of human subjects 10.

Figure 1C:
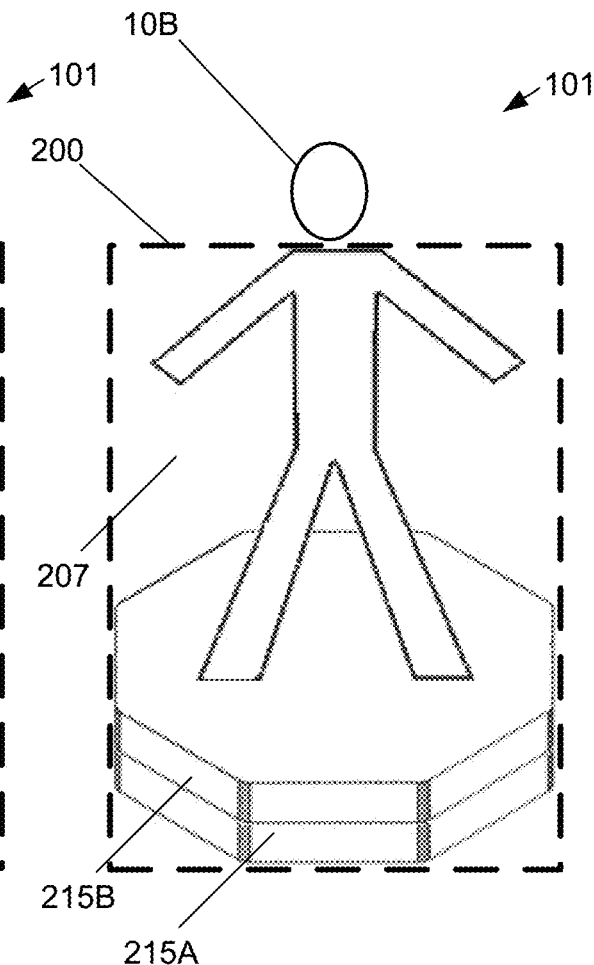
FIG. 1C illustrates one exemplary embodiment of two risers used to support a human subject within a cryogenic chamber of a whole body cryotherapy system.

FIG. 1C illustrates one exemplary embodiment of two risers to 215A, 215B used to support a human subject 10B within a cryogenic chamber 200 of a whole body cryotherapy system 101. In this exemplary embodiment, two risers 215A, 215B are employed because the human subject 10B has a height which does not allow the head of the human subject 10B to protrude above the removable cover 210.

Each riser 215 may have a predetermined height/thickness such as on the order of inches. For example, each riser 215 may have a height/thickness that may range between about 2.0 inches to about 12.0 inches. However, other heights/thicknesses are possible are included within the scope of this disclosure. Each riser 215 may have a shape that substantially mirrors or is identical to the cross-sectional shape of the cryogenic chamber 200. In other exemplary embodiments, each riser 215 may have a different cross-sectional shape relative to the cross-sectional shape of the cryogenic chamber to 200. Further, each riser 215 may also have a different height/thickness relative to another riser 215.

Each riser 215 may be made of a uniform material or a plurality of different materials. According to one exemplary embodiment, each riser 215 may be constructed from plastic materials. For example, each riser 215 may be constructed from expanded polyethylene foam high-density polystyrene covered with an antimicrobial, antibacterial, and water resistant fabric. The unique combination of risers in the chamber 200 allows for quick change in height adjustment for human subjects 10. There are no moving parts for the risers 215, so there typically is no possibility of a human subject 10 "dropping" while standing on the risers. Such a drop may occur when conventional chambers lose power while using electrical/adjustable/pneumatic floor jacks to adjust for the heights of human subjects 10.

Figure 1D:
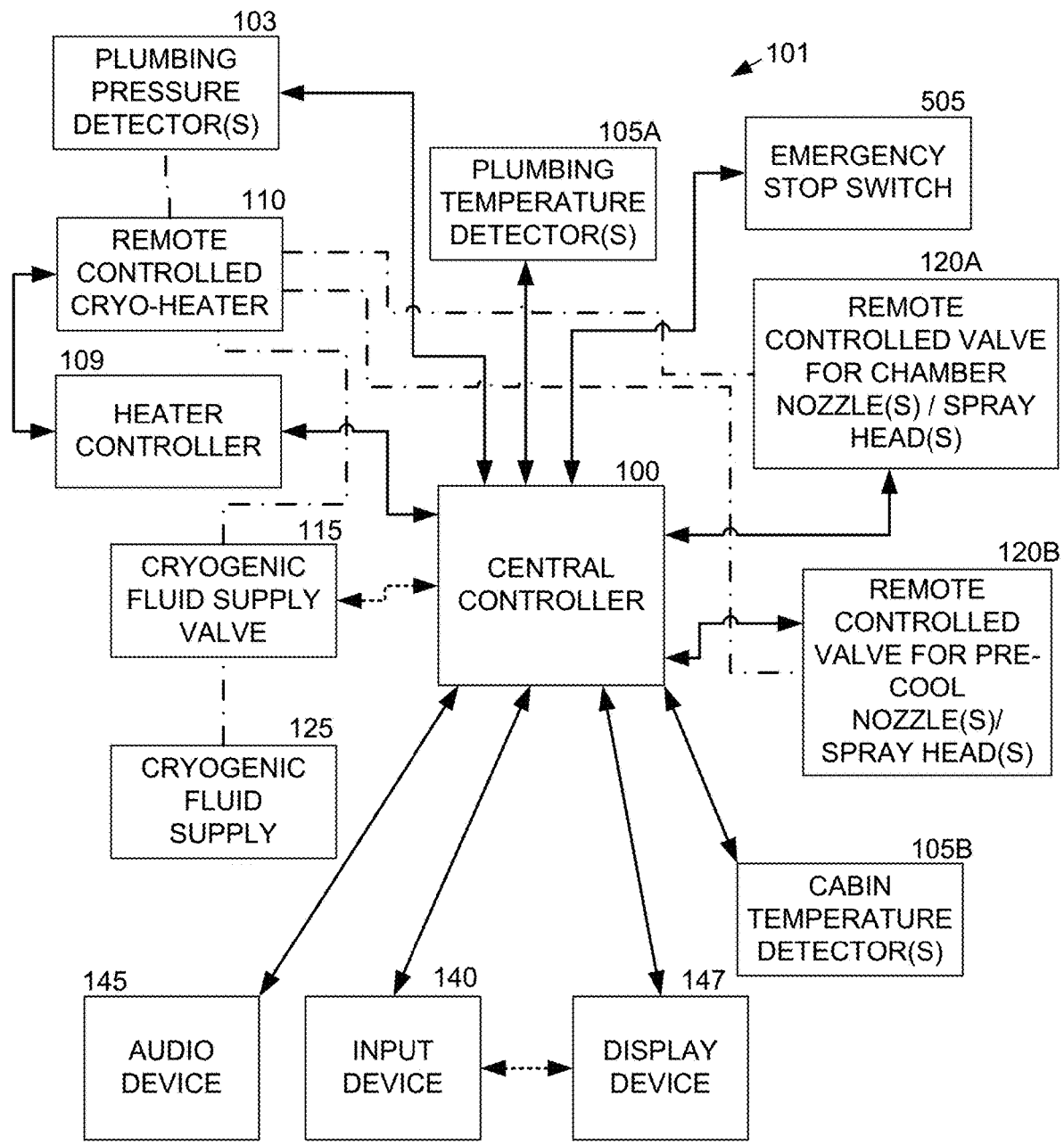
FIG. 1D is a functional block diagram illustrating the central controller and its associated subcomponents of the system for providing whole body cryotherapy.
Figure 22:
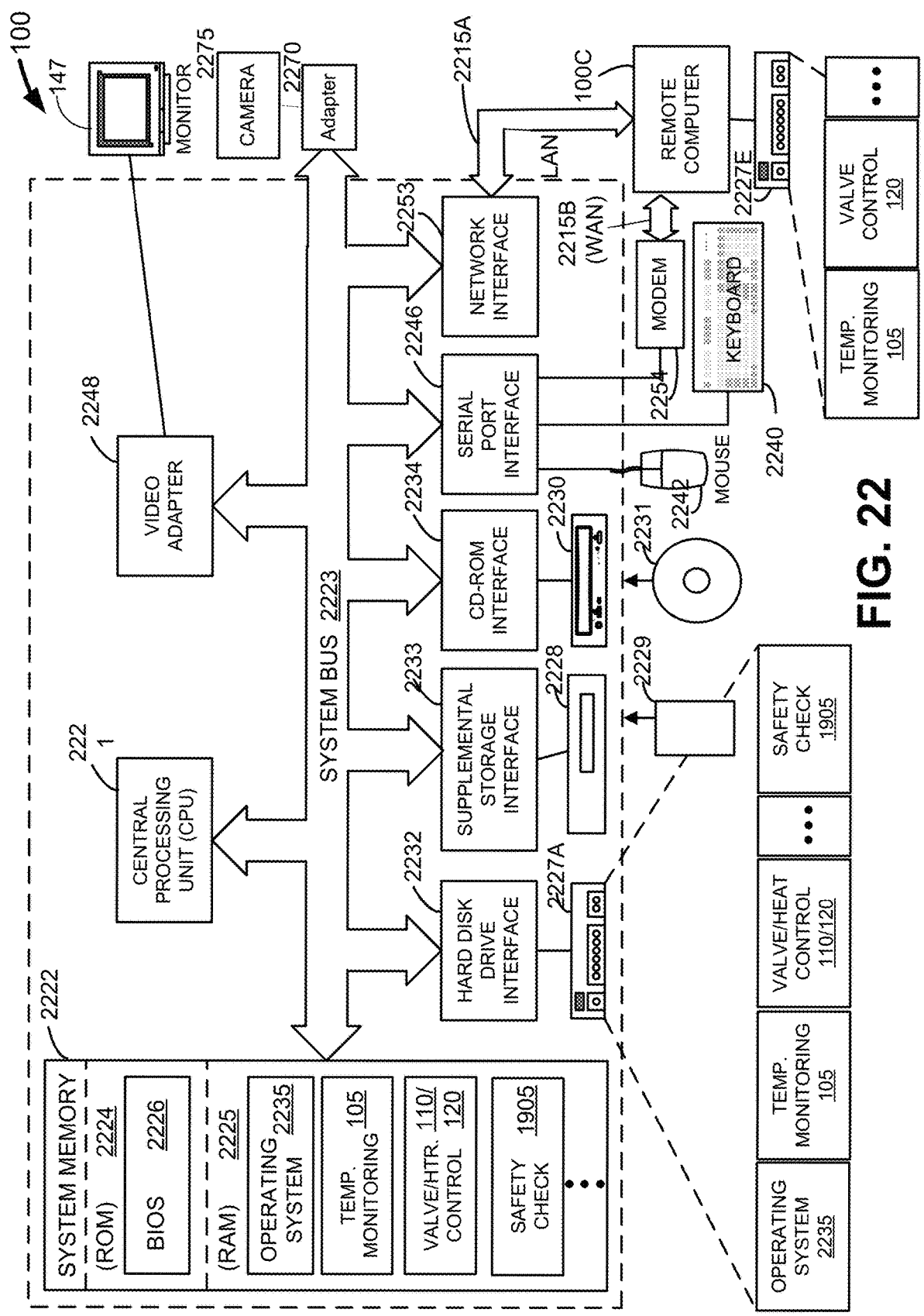
FIG. 22 is a functional block diagram of an internet connected computer that may embody/form the electronic central controller discussed above according to an exemplary embodiment of the invention.

FIG. 1D is a functional block diagram illustrating a central controller 100 and its associated subcomponents of the system 101 for providing whole body cryotherapy. The central controller 100 may comprise hardware and/or software or any combination thereof. The central controller 100 may comprise a Programmable Logic Controller (PLC) and/or a special purpose computer used for automation of commercial or industrial electromechanical processes. However, one of ordinary skill in the art recognizes that a general purpose computer (such as illustrated in FIG. 22) may be employed and may become "special purposed" when it executes the software and/or hardware functions described below. Exemplary PLCs available as of this writing and that may be used for the central controller 100 include those made by ProFace America, model PFXLM4301TADAC.

The central controller 100 may be responsible for adjusting the temperature within the volume 207 defined by a cryogenic chamber 200. The central controller 100 may monitor the temperature of the cryogenic chamber 200 as well as monitoring the pressure of the cryogenic fluid. The central controller 100 may actively control the flow of a cryogenic fluid used to cool the chamber 200 before and during a cryogenic therapy session. The central controller 100 may provide data to a human operator that may include the current temperature within the cryogenic chamber 200, pressure of the cryogenic fluid, as well as the options for selecting time limits associated with predetermined levels of different types of cryotherapy sessions. The central controller 100 may relay its data through the display device 147 and/or audio device 145 such as a speaker.

The central controller 100 may also receive commands and/or data through an input device 140. This input device 140 may comprise a keypad or keyboard or a touch screen display device 147. While the input device 140 and display device 147 are displayed as two different elements in FIG. 1D, one of ordinary skill in art recognizes that these two devices may be combined or part of a single device such as a touch-screen display.

Further, the input device 140 and the display device 147 could take the form of a portable computing device such as a mobile phone or a tablet PC as understood by one of ordinary skill the art. In such an exemplary embodiment, the portable computing device comprising the input device 140 and the display device 147 may be coupled to the central controller 100 in a wireless manner as understood by one of ordinary skill the art. Such a portable computing device may be coupled to the central controller 100 via a computer communications network, such as the Internet.

The central controller 100 may be coupled to a heater controller 109 (which is coupled to a cryogenic heater 110), one or more plumbing pressure sensors 103, one or more plumbing temperature detectors 105A, one or more remote controlled valves 120A that are coupled to cabin spray heads, one or more remote controlled valves 120B that are coupled to pre-cool spray heads, and one or more temperature detectors 105B1. As noted above, the central controller 100 may also be coupled to an input device 140, an audio device 145, and a display device 147.

According to an alternate exemplary embodiment, the central controller 100 may also be coupled to one or more remote controlled cryogenic fluid supply valves 115. However, in other exemplary embodiments, the cryogenic fluid supply valves 115 may be manual in nature and require activation thereof by a human operator. The cryogenic fluid supply valves 115 may be coupled to a cryogenic fluid supply 125.

The cryogenic fluid supply 125 may comprise a container that holds the cryogenic fluid. According to one exemplary embodiment, the cryogenic fluid for producing cryogenic temperatures within the cabin or chamber 200 may comprise liquid nitrogen. However, other types of cryogenic fluids may be used without departing from the scope of this disclosure. Other cryogenic fluids include, but are not limited to, argon (AR), helium (He), oxygen (O), and hydrogen (H). But those cryogenic fluids which are highly flammable, such as oxygen and hydrogen, are usually less favored because of the risks associated with their flammable properties.

The container for the cryogenic fluid supply 125 may comprise a 230-liter low pressure (typically about 22.0 to 23.0 psi) tank that is commercially available through industrial gas suppliers throughout the United States. The plumbing system 800 (See FIG. 8A) of the chamber 200 is linked to the low-pressure tank 125 typically through a 0.5 inch inside diameter by about a six (6) foot long cryogenic hose that has one 45 Degree Female SAE Connection on each end. The working temperature that the hose can withstand is a range usually from about −321.0 degrees F. to about +500.0 degrees F. and the maximum working pressure the hose can sustain is about 500.0 PSI.

The elements of the cryogenic fluid supply 125, the cryogenic fluid supply valve 115, remote-controlled cryogenic heater 110, the remote-controlled valve 120 for the cabin spray heads, and the remote-controlled valve 120B for the pre-cool spray heads have been illustrated as connected with the dashed line. This dashed line represents one exemplary coupling of these elements via conduits (or "plumbing") 810 (see FIG. 8A) as described in further detail below in connection with FIG. 16A.

The remote-controlled cryogenic heater 110 may comprise an electrical heating element designed to heat up the cryogenic fluid from the cryogenic fluid supply 125 if the temperature of the cryogenic fluid is not at a predetermined temperature when exiting one or more of the cabin spray heads during a cryotherapy session. The predetermined temperature is one that is about at or above—192.0 degrees Celsius. If the temperature of the cryogenic fluid exiting a cabin spray head is below this predetermined temperature (meaning that the cryogenic fluid is too cold for a cryogenic therapy session), then the central controller 100 may send commands to the heater controller 109 which in turn sends commands to the remote-controlled cryogenic heater 110 in order to warm or heat the cryogenic fluid to reach the predetermined temperature.

The heater 110 may comprise a 400 Watt, 120 Volt heater that is designed to add heat the cryogenic fluid, such as liquid nitrogen, using internal heating elements without adding external airflow meaning that all of the additional mixing and heating of cryogenic fluid occurs within a heater core element. According to one exemplary embodiment, the heater 110 may comprise one that is manufactured by OMEGA, model number AHPF-061.

The heater controller 109 may comprise an overheat/high temperature safety circuit built into the heater 110. When the temperature of the heater 110 exceeds about 190.0 degrees F., the heater controller 109 may shut down (turn off electrical power to) the heater 110. The heater controller 109 may also comprise a circuit/hardware that may alert the central controller 100 if the heater 109 is not functioning properly. According to one exemplary embodiment, the heater controller 109 may comprise a monitoring relay that may be tapped into a 120 VAC wire past a main heater relay circuit.

When the monitoring relay of the heater controller 109 "sees"/determines that a voltage threshold had been met, it may close the circuit preventing power to the heater 110 and then transmit a message to the central controller 100. If the heater 110 is supposed to be on and the central controller 100 does not receive a message from the heater controller 109 (where the message may comprise a 24 VDC signal), the central controller 100 may shut down all its slaves/devices and it may display a heater failure message that is illustrated in FIG. 18E described in further detail below.

Each of the temperature detectors 105 may comprise electrical resistance temperature detectors (RTDs) as understood by one of ordinary skill the art. Exemplary RTDs available as of this writing include ones manufactured by Pyromation, Inc and are designed to have about a 3.5" hot leg, 2.5 cold leg, and 90-degree bend. The Pyromation model number for their RTDs are 1005612. However, other temperature detectors/sensors 105 may be employed without departing from the scope of this disclosure. Other types of temperature detectors/sensors 105 may include, but are not limited to, electromechanical and electronic types which may encompass bimetallic thermostats, as well as thermocouples. Exemplary resistance temperature detectors 105 may comprise one or more thermistors as understood by one of ordinary skill the art.

Each plumbing pressure sensor 103 may comprise a pressure transducer. Exemplary transducers may include, but are not limited to, transducers manufactured by Turk, model number PT100PSIG-13-LI3-H1131, as of this writing.

Each plumbing pressure sensor 103 may monitor the pressure in the plumbing 810 (see FIG. 16A) and may send pressure information to the central controller 100. The "normal" or typical working pressure maintained in the plumbing 810 may comprise a range between about 18.0 pisg to about 30.0 psig. When pressure is monitored in this "normal" range by a plumbing pressure sensor 103, the central controller 100 may allow a standard/normal cryotherapy session to be run and the central controller 100 may send a "normal" range message as illustrated in FIG. 18B (described below) to the display device 147.

Figure 18A:
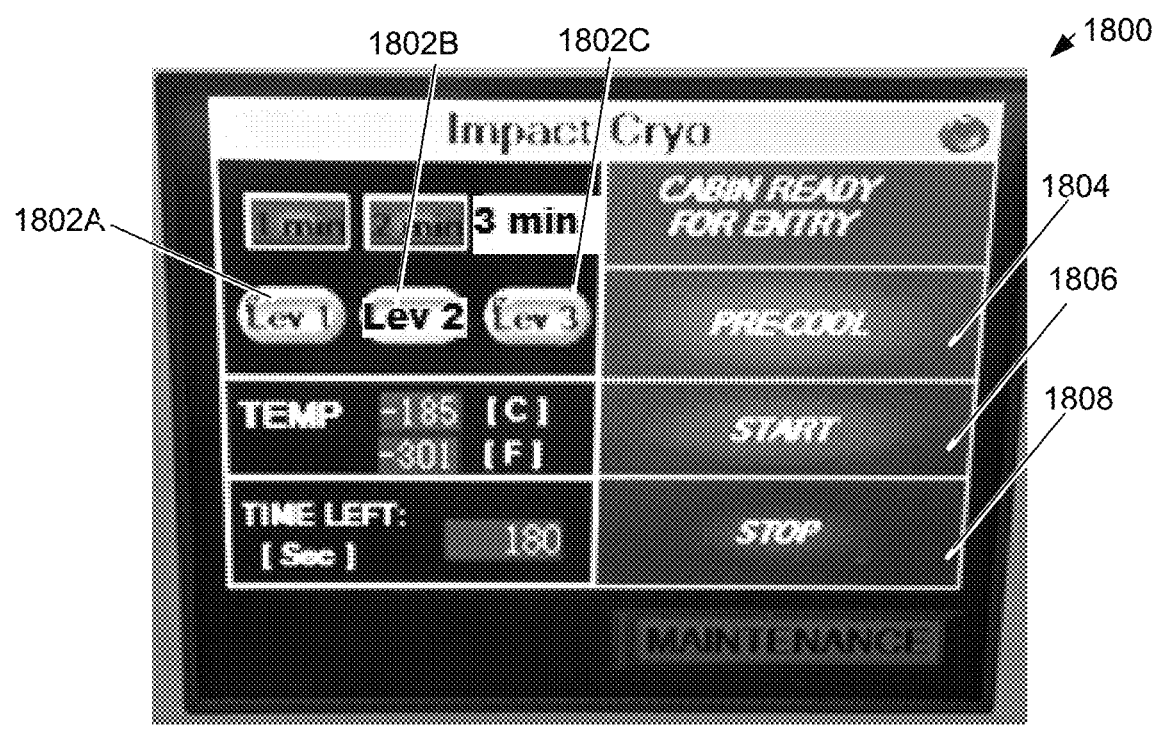
FIG. 18A illustrates one exemplary embodiment of a screen shot for the display device generated by the electronic central controller for receiving input for the options that may be selected for a cryotherapy session.
Figure 18B:
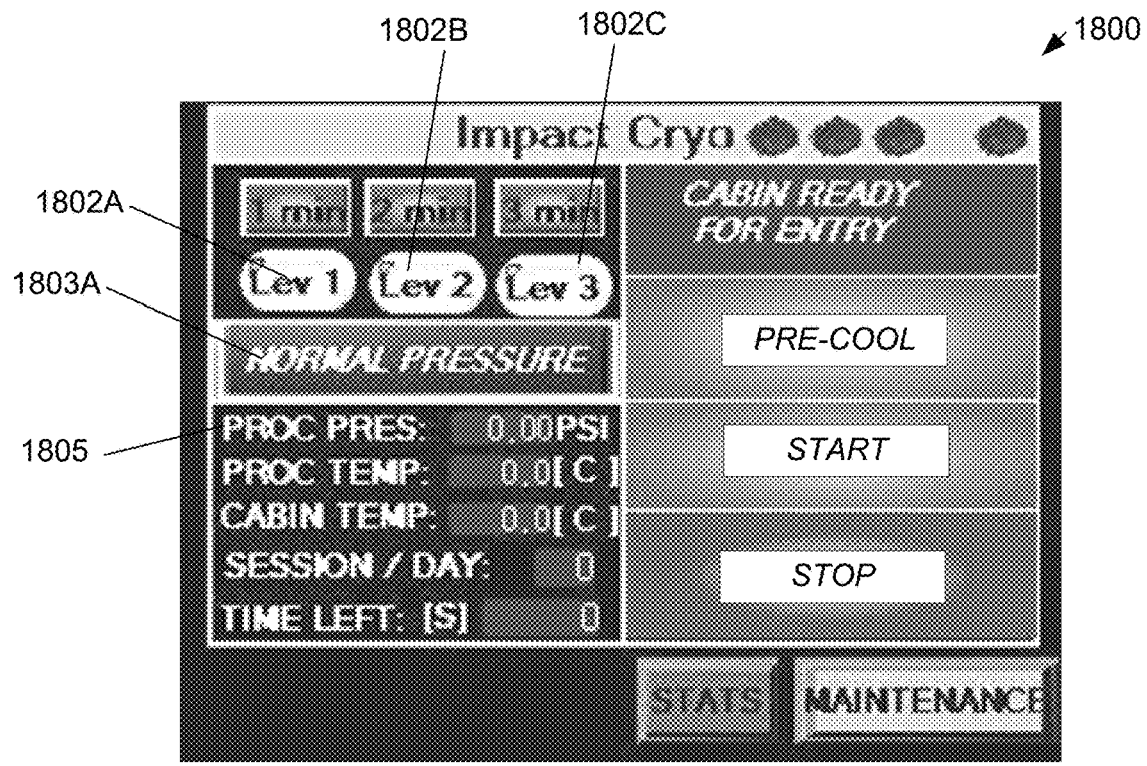
FIG. 18B illustrates another exemplary embodiment of a screen shot for the display device generated by the electronic central controller for receiving input for the options as well as displaying a pressure message for a cryotherapy session.
Figure 18C:
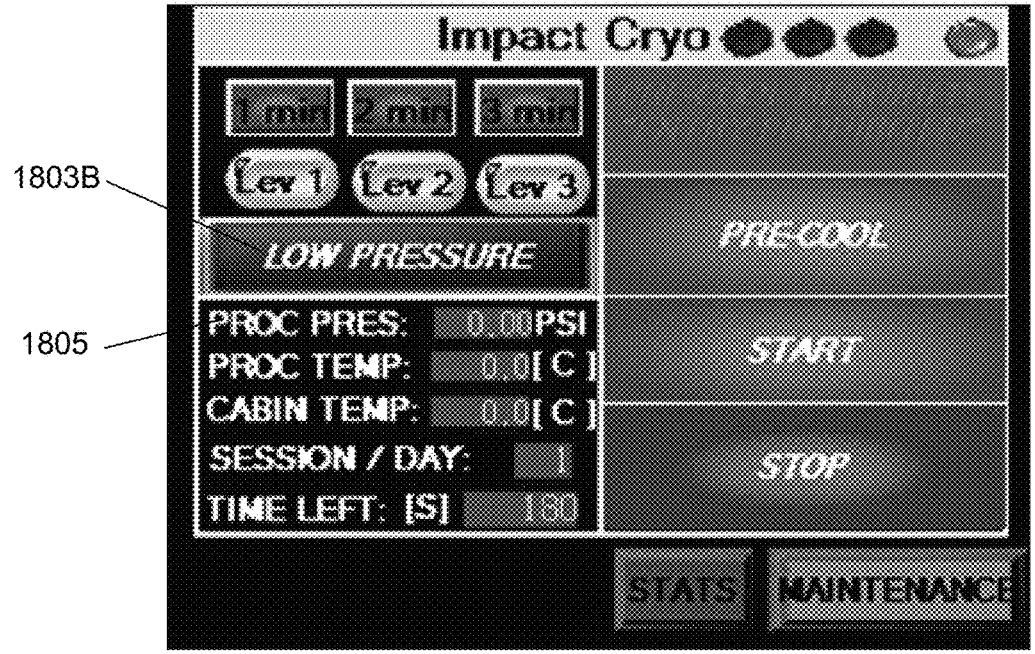
FIG. 18C illustrates another exemplary embodiment of a screen shot for the display device generated by the electronic central controller in which a low pressure message is displayed.

When central controller 100 receives an input signal from a plumbing pressure sensor 103 that is lower than the "normal operating pressure range," the central controller 100 may change the normal pressure message as illustrated in FIG. 18B to a low pressure message as illustrated in FIG. 18C (described in further detail below).

When the low pressure message of FIG. 18C is displayed on the display device 147, the system will continue to operate, however, the low pressure condition may lead to an ineffective cryotherapy session. The pressure in the plumbing 810 (as illustrated in FIG. 16 described below) is required to be in a specific range of pressures to operate the cryochamber effectively and efficiently.

Figure 18D:
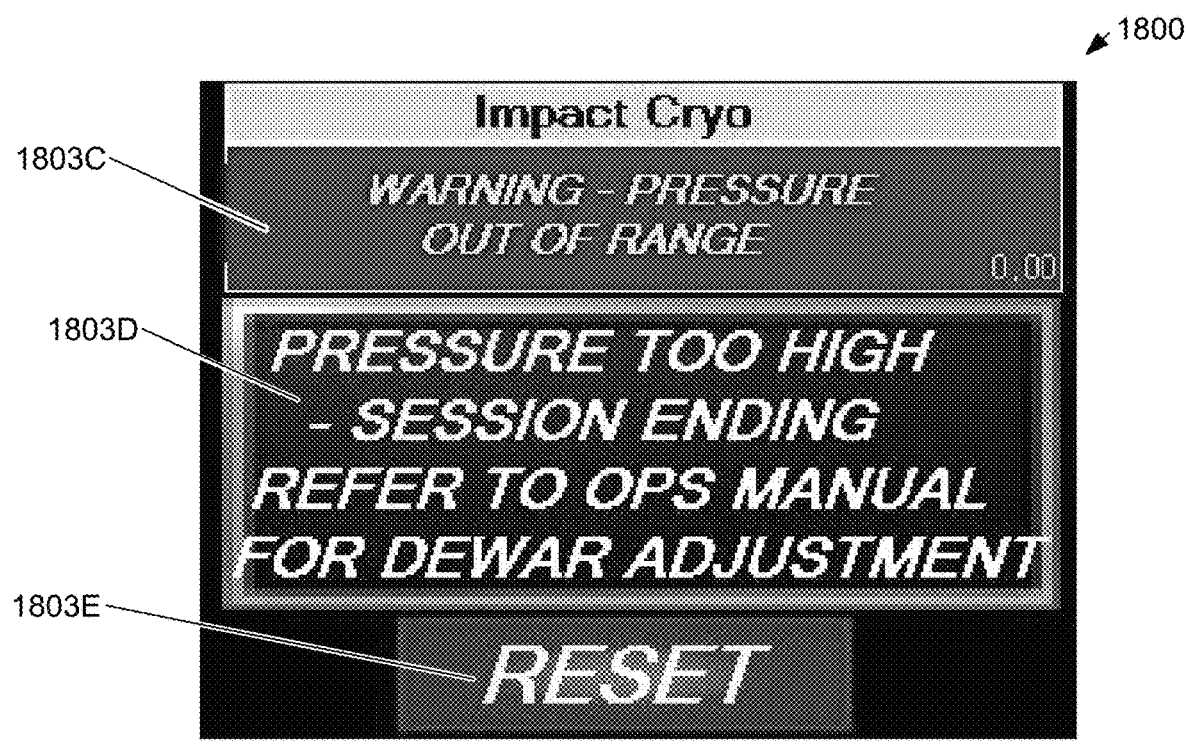
FIG. 18D illustrates another exemplary embodiment of a screen shot for the display device generated by the electronic central controller in which a high pressure message is displayed.
Figure 18E:
FIG. 18E illustrates another exemplary embodiment of a screen shot for the display device generated by the electronic central controller in which a heater failure message is displayed.

One exemplary pressure range for operating the cryochamber effectively and efficiently may comprise between about 18.0 psig and about 30.0 psig. In the event that a pressure sensor 103 detects pressures that exceed about 30.0 psi, the central controller 100 displays a message on the display device as illustrated in FIG. 18D (described in further detail below) and central controller 100 may conduct a complete shutdown of the system 101 to stop the flow of the cryogenic fluid, such as, but not limited to Nitrogen, into the cryo-chamber 200. The shutdown process performed by the central controller 100 for a high pressure condition may be similar to the emergency stop condition described below that may be activated by the emergency shut-off switch 505 described below.

During a shutdown process, the central controller 100 may send a message to the remote controlled valves/solenoids 120 (120A-120B) to force them to close—if they are open and the central controller may also issue an audible message such as a "beep sound" to the audio device 145.

Each of the remote-controlled valves 120 may comprise solenoid valves as understood by one of ordinary skill in the art. The solenoid valves 120A, 120B are usually designed to work with a cryogenic fluid, such as liquid nitrogen, at about −194.0 degrees Celsius, and with ambient environment temperatures up to about +150.0 degrees F. Exemplary remote-controlled valves 120 available as of this writing are REGO brand cryovalves, model number BK9453.

According to one exemplary embodiment, each remote-controlled valve 120 may comprise a ⅜ inch two-way solenoid valve and in which the actuator is manufactured by ASCO REDHAT, model number 8263H125LT. However, other manufacturers may be employed without departing from the scope of this disclosure.

Each remote-controlled valve 120 is normally closed—meaning that the fluid/gas is shut off when its solenoid coil is de-energized. When the solenoid is energized/powered by the central controller 100, the valve is open and fluid/gas is allowed to flow through the valve. This is a safety related portion of the system 101 and is intended to cutoff liquid the cryogenic fluid or gas (such as liquid nitrogen and/or nitrogen gas) in the event of loss of power or signal to the solenoid valve 120. While the solenoid valves 120 may operate using electricity, other types of actuation are possible such as pneumatic type valves.

Each solenoid valve 120 is also direct acting which means that when the solenoid of a valve 120 is energized, the core valve opens the orifice of the normally closed valve. Each remote-controlled valve 120 may be rated to work at various pressure levels, from about 0.0 psi to a maximum Operating Pressure Differential (OPD) of about 40.0 psi.

The cryogenic fluid supply valve 115 may comprise a Rego Cryo Valve (Cryo Valve) that is attached on one end to the remote controlled heater 110 and on the other end to a cryogenic insulated hose that is connected to the cryogenic fluid supply 125, that may include a source tank of liquid nitrogen.

The cryogenic fluid supply valve 115 may contain two ½ inch fittings—one on each end as understood by one of ordinary skill the art and may be rated for a maximum working pressure of about 600.0 psi. The cryogenic fluid supply valve 115 may be one that is manufactured by REGO, model number BK945. The cryogenic fluid supply valve 115 it its stem may be specifically designed to operate at super-low cryogenic temperatures. As the plumbing/conduit system is assembled (See FIG. 16), the cryogenic fluid supply valve 115 may be attached to a stainless steel tube via specialized cryogenic type fittings. Fittings may include, but are not limited to, Elbows, Unions, Tee/Cross, Reducers and other compression fitting connectors.

As noted previously, the cryogenic fluid supply valve 115 may comprise one that is manually operated according to one exemplary embodiment. In other exemplary by limits, a remote controlled valve 120 may be substituted for the cryogenic fluid supply valve 115 such that the central controller 100 may send control signals two the remote-controlled valve 120.

The central controller 100 may be responsible for preparing the chamber 200 for cryotherapy sessions as well as monitoring and maintaining cryotherapy sessions for a human subject 10. The central controller 100 may provide safety features such as requiring feedback from a human operator of the system 101 while a cryotherapy session is underway for a particular human subject. Further details of the safety features as well as different types of cryotherapy sessions that may be selected with the central controller 100 described in further detail below in connection with the screen displays of FIGS. 17-20. The central controller may also monitor an emergency off switch 505. The emergency off switch 505 may be electrically coupled to the central controller 100. Additionally, the emergency off switch 505 may also be coupled directly to all electrical power systems and may cut off electricity to the entire system 101 including the central controller 100 in some embodiments.

Figure 2:
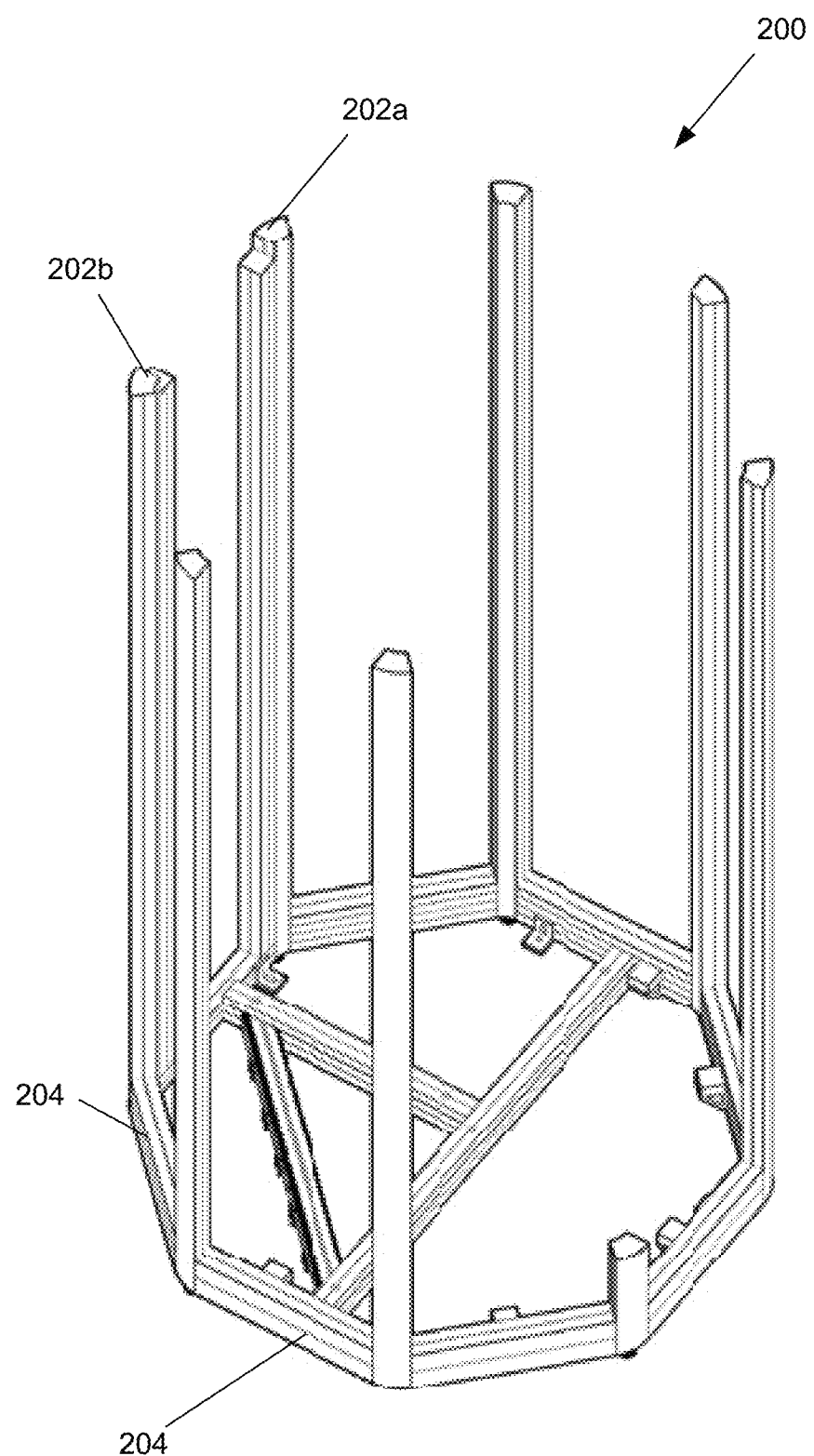
FIG. 2 illustrates one exemplary support frame used to construct the cryogenic chamber illustrated in FIG. 1A.

Referring now to FIG. 2, this figure illustrates one exemplary support frame used to construct the cryogenic chamber 200 illustrated in FIG. 1A. While the cryogenic chamber 200 is illustrated as having an octagonal shape, other shapes are possible and are within the scope of this disclosure. Other shapes include, but are not limited to, rectangular, square, circular, pentagonal, hexagonal, elliptical, etc.

The cryogenic chamber 200 may be constructed with T-Slot black anodized aluminum extrusions held together with T-slot connectors as understood by one of ordinary skill the art. The extrusions may be cut to engineered specifications and cut lengths. Once sized and cut, the cryogenic chamber 200 is generally built from the base—or bottom support ring 204, upward.

The bottom support ring (commonly referred to as the "lower ring") 204 may be assembled and hardware/fasteners are installed in the aluminum extrusions of the support ring 204 so that upright supports 202 may be attached to the lower ring 204. Typical fasteners that may be used are metal bolts and T-nut or Z-nut fasteners. However, other fasteners may be employed such as screws or rivets. The uprights 202 may be fabricated from lengths of anodized extruded aluminum bars and cut to size per engineering specifications and lengths as desired. Once the quantity of uprights 202 are fabricated, the uprights 202 are installed per engineering specifications and locations taking special care to note the entrance door 202 and back box/Accessory box 602 (see FIG. 6 for back box 602).

Figure 3:
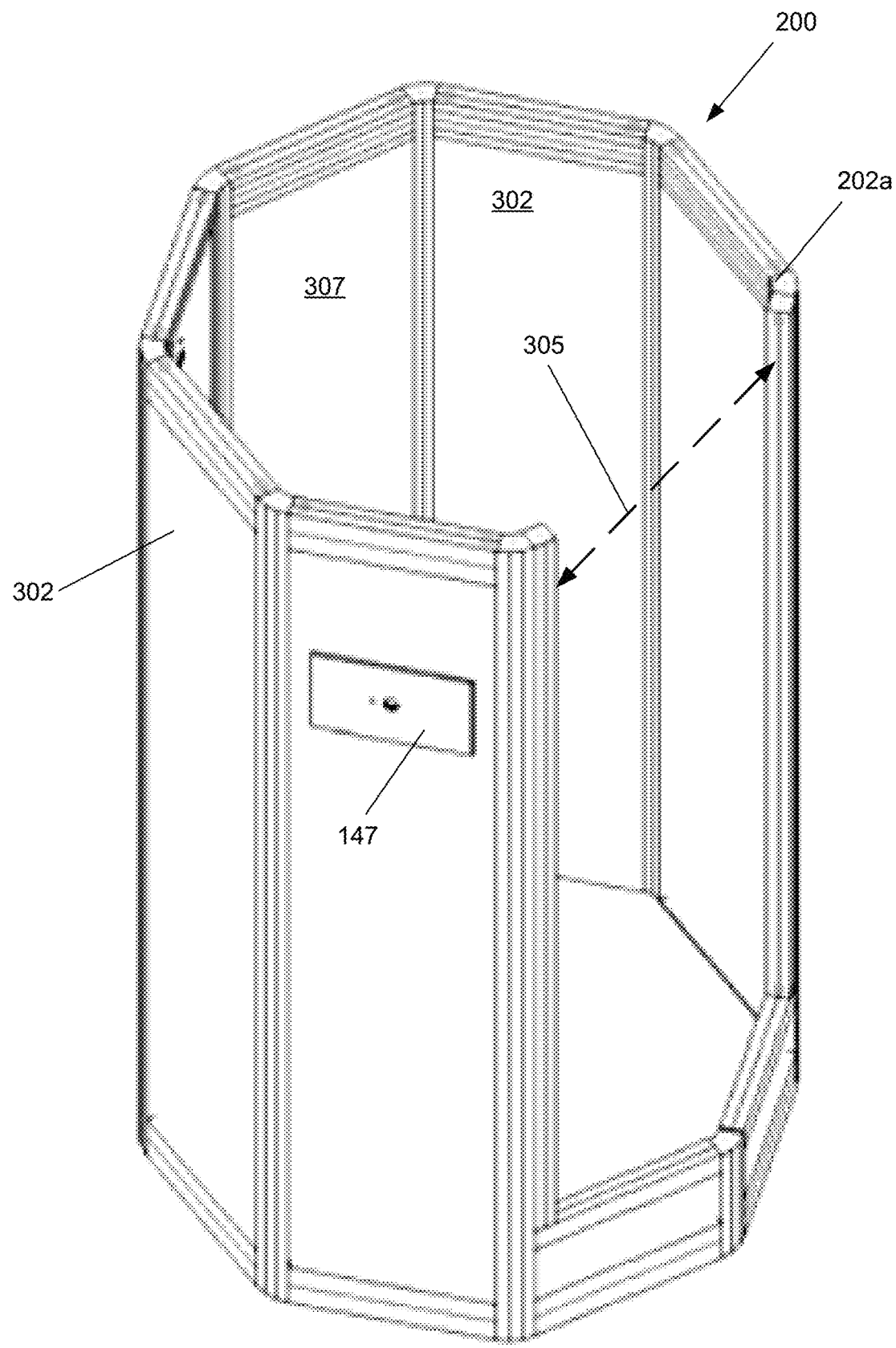
FIG. 3 illustrates one exemplary embodiment of a partially assembled cryogenic chamber used in FIG. 1A.

FIG. 3 illustrates one exemplary embodiment of a partially assembled cryogenic chamber 200 used in FIG. 1A. The chamber 200 may be formed by panels 302 that are positioned between the uprights 202. According to one exemplary embodiment, the panels 302 may be constructed from a plastic material, such as, but not limited to acrylic. However, other materials for panels 302 are possible and are included within the scope of this disclosure. Other materials for the panels 302 may include, but are not limited to, metal, ceramics, wood, composites, or any combination thereof.

A specially machined aluminum panel 307 may be positioned at the rear of the chamber 200. The special aluminum panel 307 may secured with between the uprights 202 by the use of silicone rubber panel gasket that is inserted between the frame members 202 and the aluminum panel to ensure a gas-tight fit of the panel in the frame formed by the uprights 202.

Figure 6:
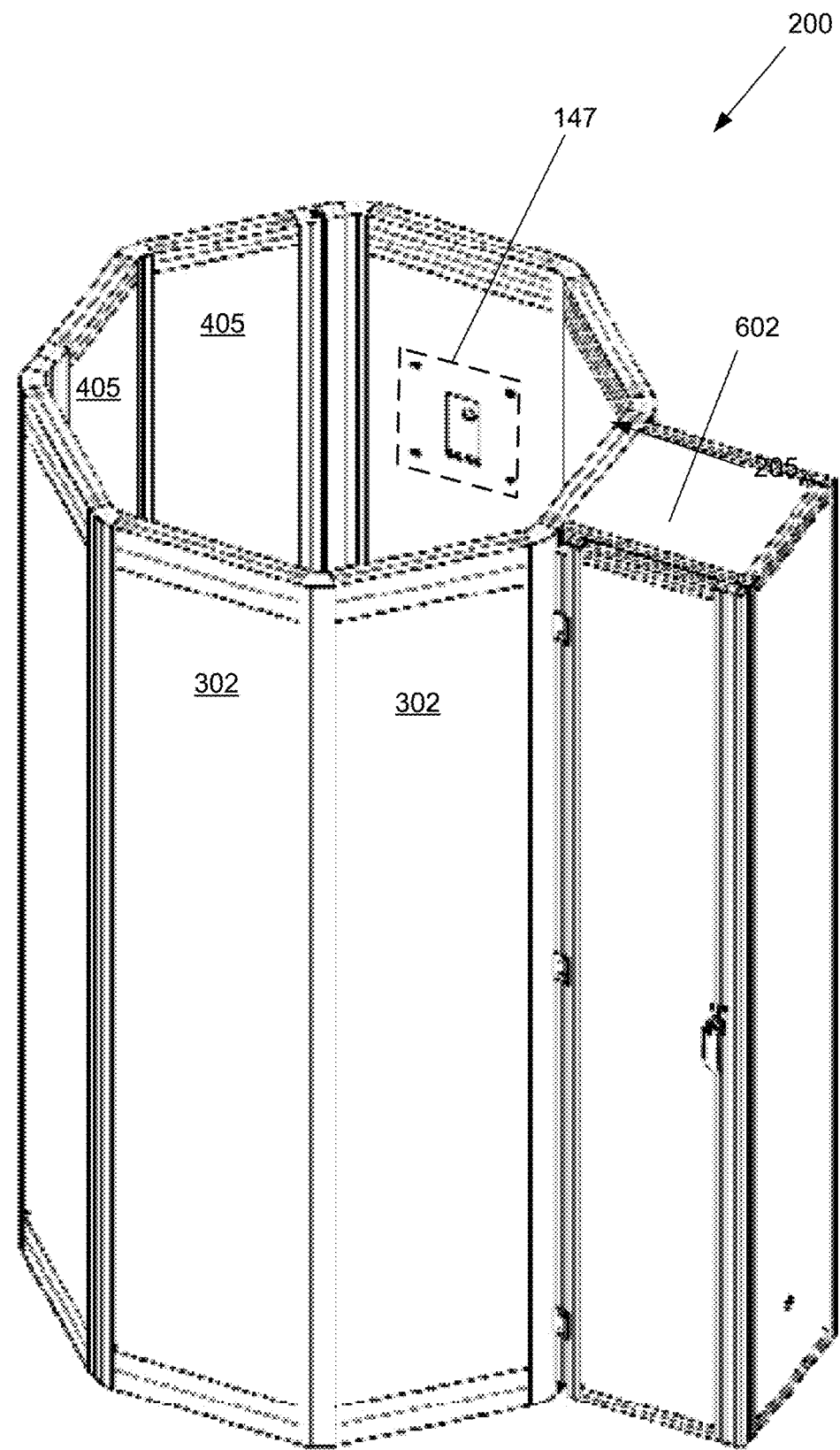
FIG. 6 illustrates one exemplary embodiment of a fully assembled cryogenic chamber coupled to a back box.

The aluminum panel 307 may form one side of the back box 602 as illustrated in FIG. 6. The other panels 302 may be secured between the uprights 202 in a similar fashion as the special aluminum panel 307 by use of silicon rubber panel gaskets that are inserted between the frame formed by the uprights 202 and the panel 302 to ensure a gas-tight fit of each panel 202 in the frame formed by the uprights 202.

An opening or side lacking any panel 302, 307 is formed as denoted by line 305. Line 305 defines a region in which the door 205 of FIG. 4 will be attached to the chamber 200 in order to form a closed volume 207 within the chamber 200.

Figure 4:
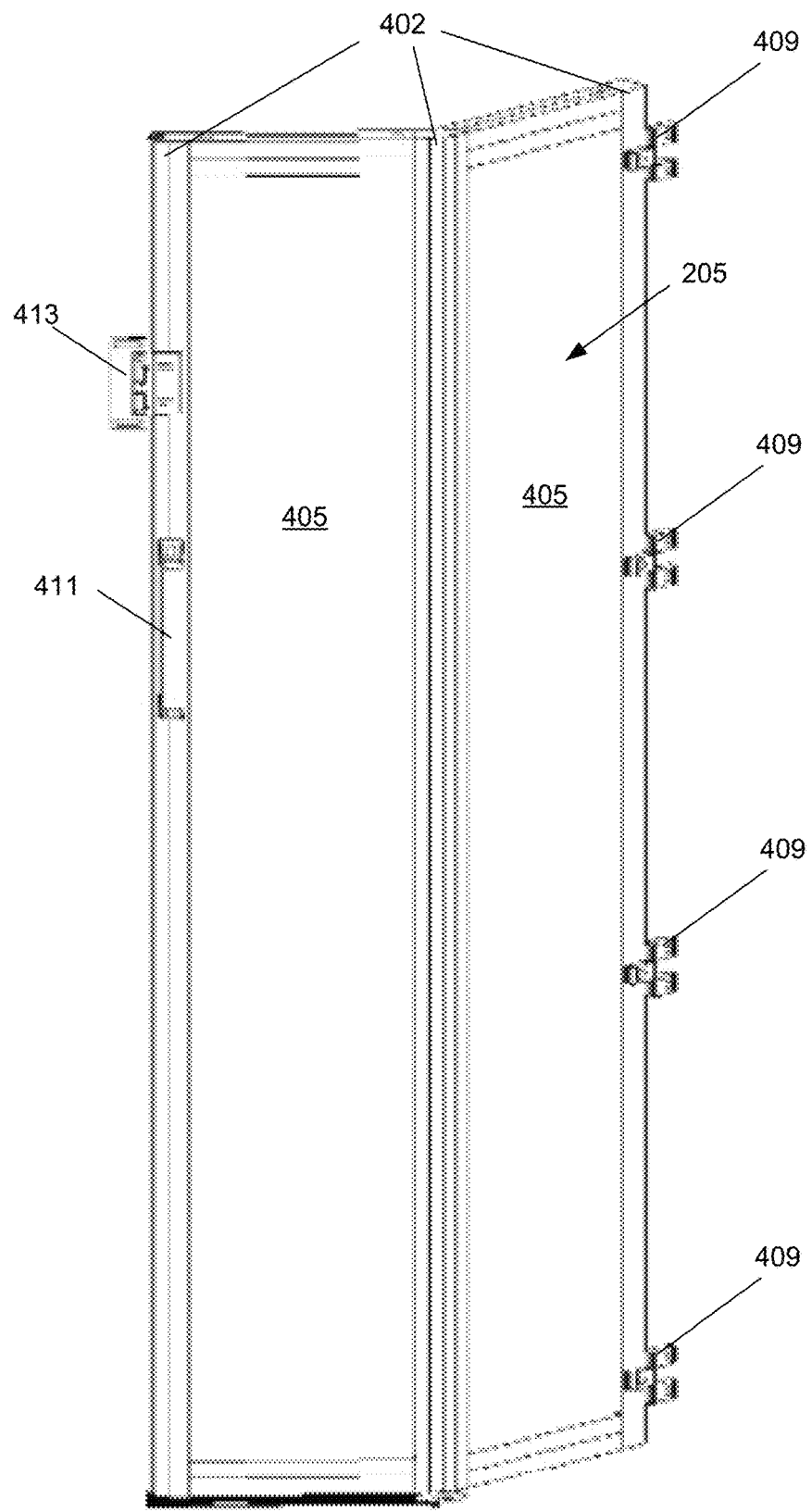
FIG. 4 illustrates one exemplary embodiment of a door for the cryogenic chamber illustrated in FIG. 1A.

Referring now to FIG. 4, this figure illustrates one exemplary embodiment of a door 205 for the cryogenic chamber 200 illustrated in FIG. 1A. The door 205 may comprise several anodized bars 402, serving as door rails and stiles. Clear, acrylic panels 405 may also be used to form the door 205. The panels 405 of the door 205 may be firmly held in place with black silicon rubber gaskets. The door 205 may be attached to the chamber 200 by using four (4) black anodized heavy-duty hinges 409. The door may have a handle 411 as well as a latch 413.

While clear panels 405 may be used in some exemplary embodiments, opaque panels 405 may also be used as desired. In the exemplary embodiment of FIG. 4, the panels 405 of door 205 may also have sizes/dimensions such that each panel 405 is substantially similar or identical in size to the panels 302 of FIG. 3. However, it is possible to form a door 205 where the panels 405 have a different size relative to the panels 302 of FIG. 3.

Figure 5:
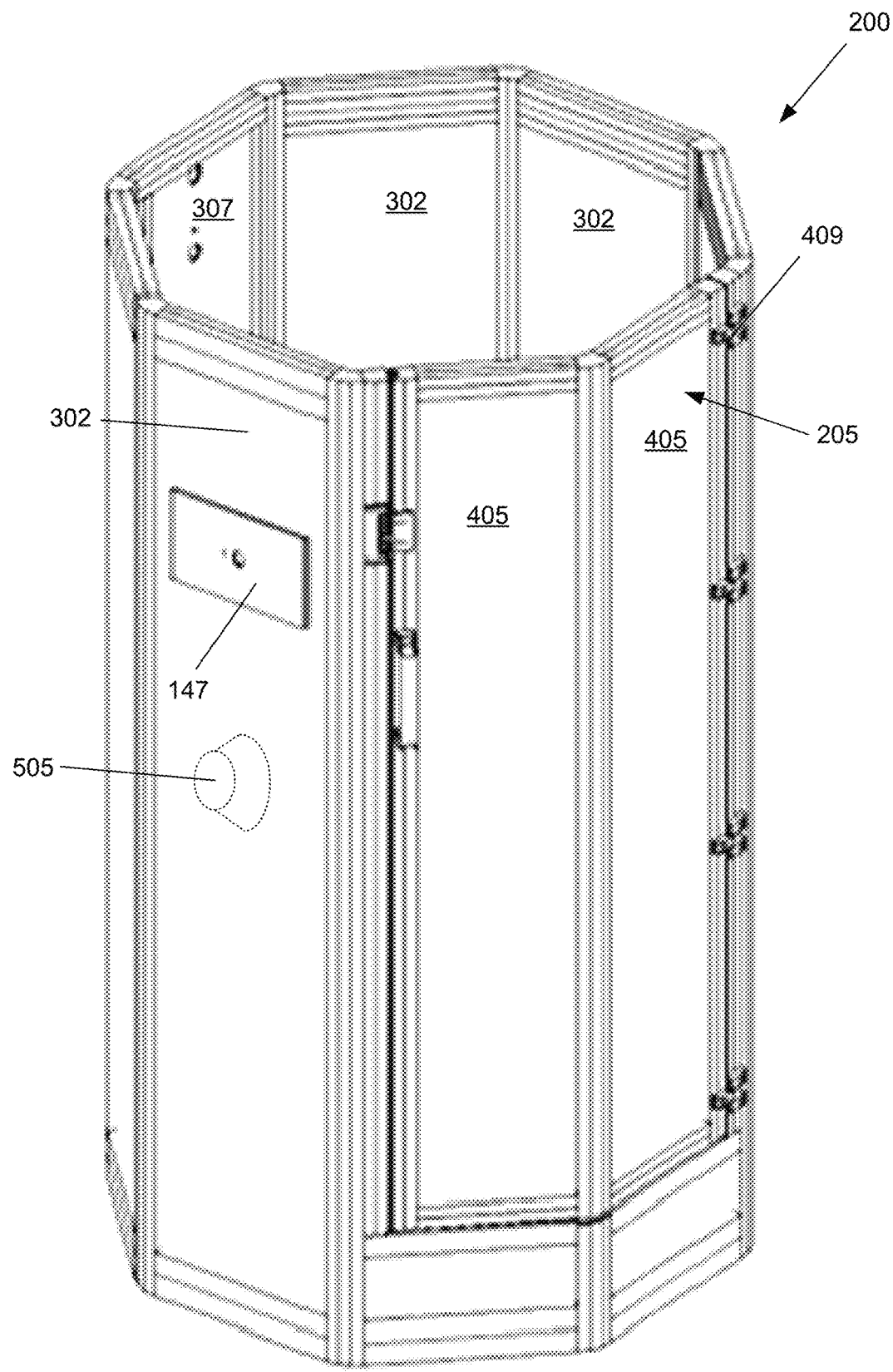
FIG. 5 illustrates one exemplary embodiment of the fully assembled cryogenic chamber of FIG. 1A with the door fully closed.

FIG. 5 illustrates one exemplary embodiment of the fully assembled cryogenic chamber 200 of FIG. 1A with the door 205 fully closed. In this view, the removable cover 210 is not shown—but see FIG. 6 described below. As previously noted, while the cryogenic chamber 200 is illustrated as having an octagonal shape, other shapes are possible and are within the scope of this disclosure. Other shapes include, but are not limited to, rectangular, square, circular, pentagonal, hexagonal, elliptical, etc.

As illustrated in FIG. 5, the emergency cut-off switch 505 described above in connection with FIG. 1D may be positioned just below the display device 147. The emergency off switch 505 is illustrated with dashed lines to indicate that it is optional and that it may be positioned anywhere within system 101 such that an operator of the system 101 may access the switch 505 to power down the system 101 in cases/situations of an emergency. This emergency cut-off switch 505 may also be positioned on a surface of the back box 602 in other exemplary embodiments as desired by the system manufacturer.

Referring now to FIG. 6, this figure illustrates one exemplary embodiment of a fully assembled cryogenic chamber 200 coupled to a back box 602. The back box 602 may house the central controller of FIG. 1D as well as other components of FIG. 1D, such as, but not limited to, the remote controlled cryogenic-heater 110, the remote controlled valve(s) 120A for the cabin spray head(s) as well as the remote controlled valve(s) 120B for the pre-cool spray heads. The back box 602 may also house the plumbing/conduits for the cryogenic fluid and the plumbing temperature detectors 105A.

Figure 7:
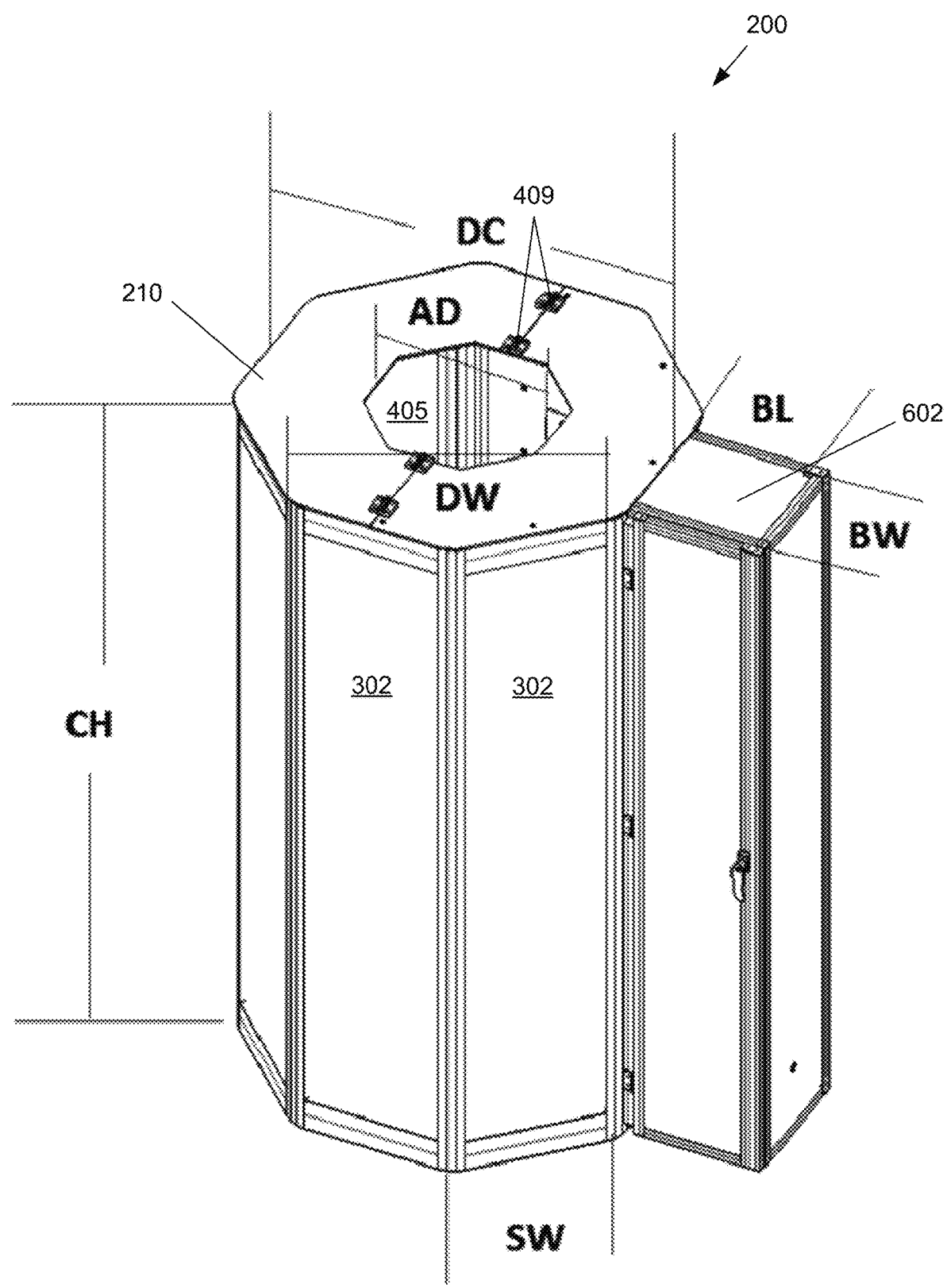
FIG. 7 illustrates one exemplary embodiment of a fully assembled cryogenic chamber coupled to a back box in addition to a top hatch that usually surrounds the neck of a human subject.

FIG. 7 illustrates one exemplary embodiment of a fully assembled cryogenic chamber 200 coupled to a back box 602 in addition to a top hatch/cover 210 that usually surrounds the neck of a human subject 10 (not illustrated in this figure). The chamber 200 may have a diameter (DC) of approximately 38.5 inches. Meanwhile, the door 205 may have a width (DW) of approximately 23.75 inches. Each side 302 of the chamber 200 may have a width (SW) of approximately 17.375 inches.

The chamber 200 may have a chamber height (CH) of approximately 70.0 inches. An aperture within a roof/cover 210 of the chamber 200 may have an aperture diameter (AD) of approximately 17.25 inches. While the aperture has been illustrated with an octagonal shape in FIG. 7, other shapes are possible and would include circular, elliptical, and the like. The back box 602 may have a back box length (BL) of approximately 13.625 inches. The back box 602 may have a back box width (BW) of approximately 13.75 inches.

However, other dimensions are possible and are included within the scope of the invention. Other dimensions for the diameter DC may include a range between about 38.5 inches and about 39.25 inches. Other dimensions for the side width (SW) may include a range between about 14.25 inches and about 15.375 inches. Other dimensions for the door width (DW) may include a range between about 23.75 inches and about 24.25 inches. Other dimensions for the chamber height (CH) may include a range between about 70.0 inches and about 75.0 inches. Other dimensions for the back box length (BL) may include a range between about 70.0 inches and about 75.0 inches. Other dimensions for the back box width (BW) may include a range between about 13.75 inches and about 14.0 inches.

Figure 8A:
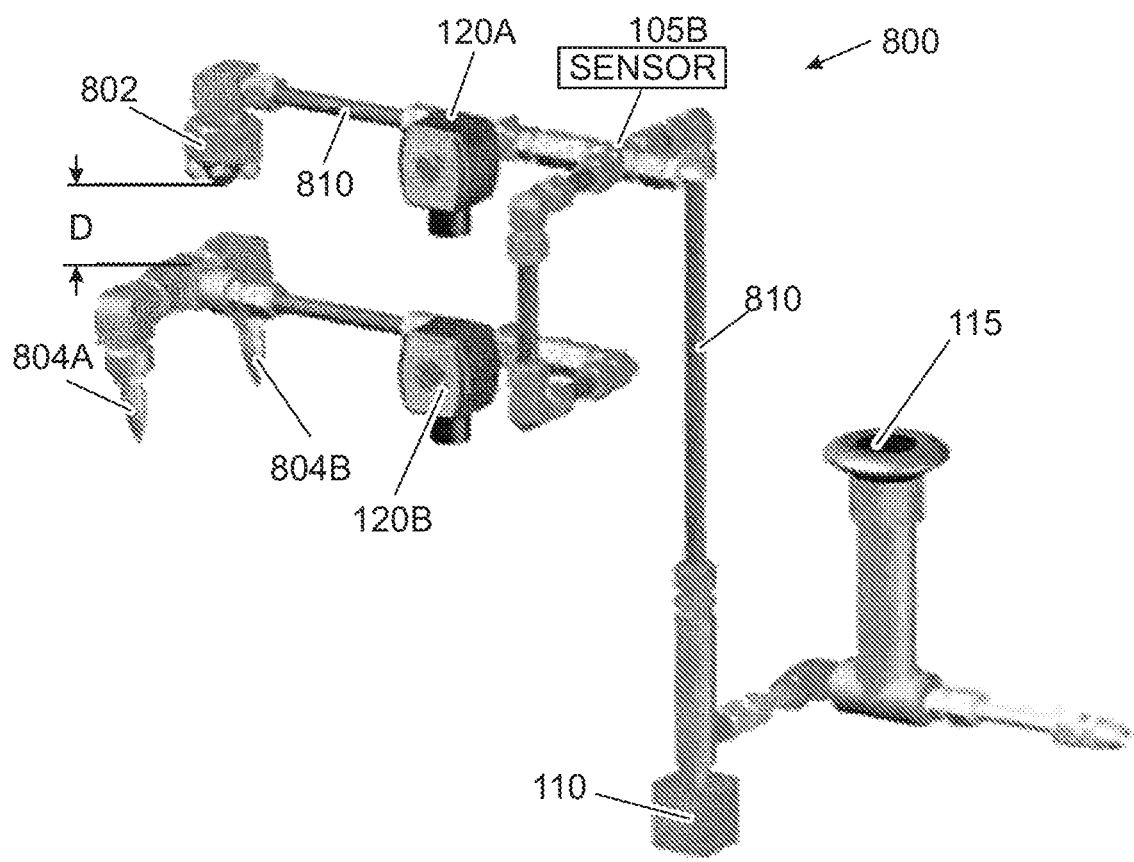
FIG. 8A illustrates a partial view of one exemplary embodiment of a plumbing system having remote controlled valves for controlling flow of liquid nitrogen for cooling the cryogenic chamber.

Referring now to FIG. 8A, this figure illustrates a partial view of one exemplary embodiment of a plumbing/conduit system 800 having remote controlled valves 120 for controlling flow of liquid nitrogen for cooling the cryogenic chamber 200. This system 800 of FIG. 8A does not comprise any pressure sensors 103 or a heater controller 109.

The plumbing conduit system may also comprise a primary spray head/nozzle 802 and a plurality of pre-cool heads/nozzles 804A, 804B. Flow of the cryogenic fluid to the primary spray nozzle 802 may be regulated/controlled by the remote controlled valve 120A as described above in connection in FIG. 1D. Similarly, flow of the cryogenic fluid to the pre-cool nozzles 804A, 804B may be regulated/controlled by the remote controlled valve 120B as described above in connection in FIG. 1D. A distance D between the cap 904 of the primary nozzle 802 and the conduit 810 that connects the pre-cool nozzles 804A, 804B together is usually between about 4.0 to about 12.0 inches, and preferably about 5.625 inches. See also FIG. 8A.

The nozzles 802, 804A, 804B may be coupled to their respective remote controlled valves 120 by conduits 810. The conduits 810 may comprise specialized pipe fittings that can be subjected to super-low temperatures, annealed copper piping, stainless steel piping, which are designed to operate at Cryogenic temperatures. The conduits 810 may comprise soft annealed copper tubes connected with specialized brass compression fittings, manufactured by Swagelok.

The remote controlled valves 120 may each be coupled to a plumbing tee-section 806 via additional conduits 810. The remotely monitored plumbing temperature detector 105A as described above in connection with FIG. 1D may be coupled to the plumbing tee-section 806.

The plumbing tee-section 806 may be coupled to the remote controlled cryogenic heater 110 by another conduit 810. The remote controlled cryogenic heater 110 may be coupled to the cryogenic fluid supply valve 115. As noted previously in connection with FIG. 1D, while the exemplary embodiment illustrated in FIG. 8 for the cryogenic fluid supply valve 115 may comprise a manually actuated/driven valve 115, one of ordinary skill in the art recognizes that a remote controlled valve 120 could easily be substituted for the manual valve so that the central controller 100 could manage its operation.

Further, one of ordinary skill in the art recognizes that the configuration/spatial arrangement of the conduit system 800 is merely exemplary and that other configurations are possible and are included within the scope of this disclosure. That is, additional conduits 810 or fewer conduits 810 may be employed without departing from the scope of this disclosure. Along these lines, the position/placement of the remote controlled valves 120 as well as the remotely monitored temperature detector/sensor 105A and remote controlled cryogenic heater 110 may be changed/adjusted for various reasons without departing from the scope of this disclosure.

Figure 8B:
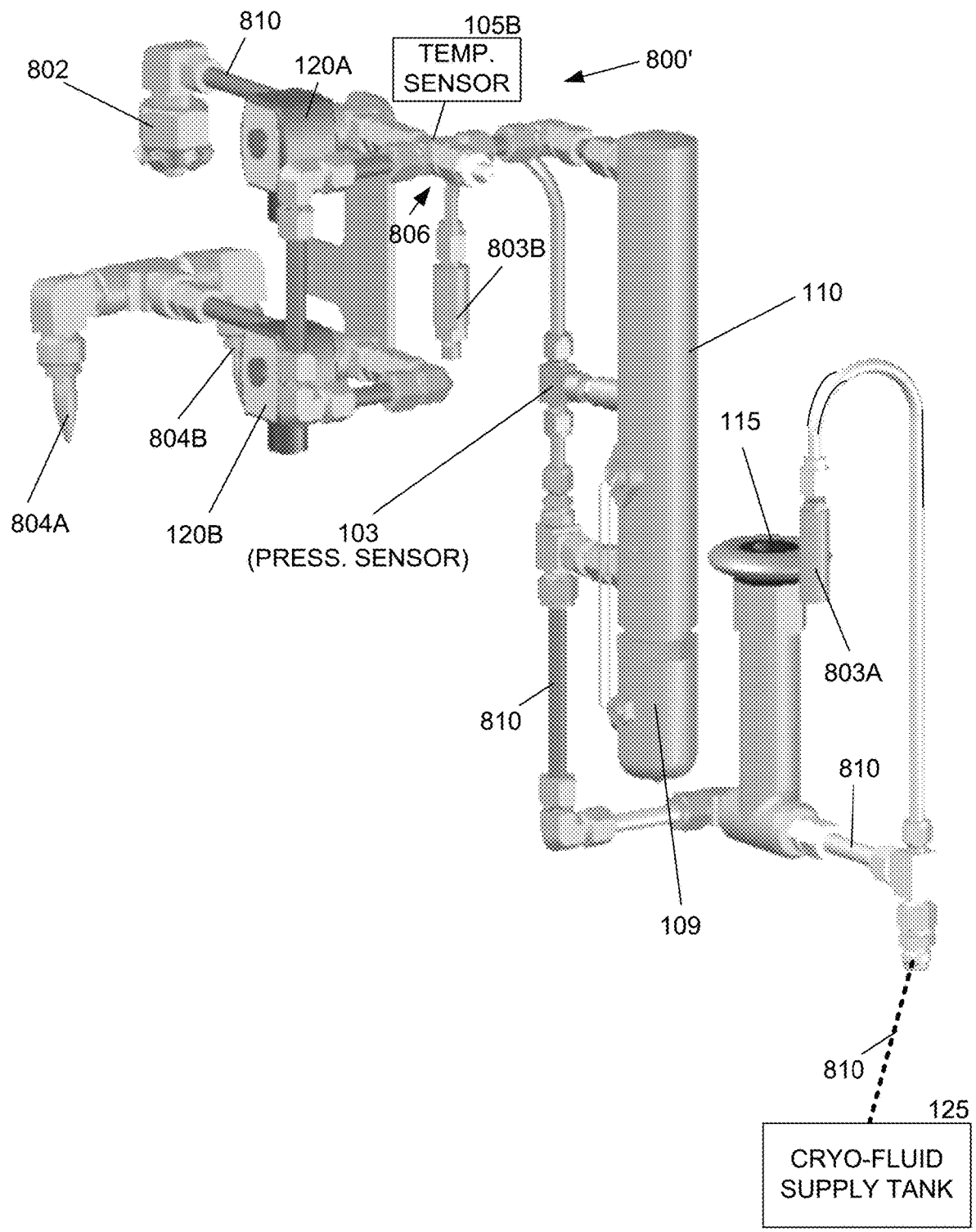
FIG. 8B illustrates a partial view of another exemplary embodiment of a plumbing system having remote controlled valves in addition to pressure sensors, pressure relief valves, and a heater controller for controlling flow of liquid nitrogen for cooling the cryogenic chamber.

Referring now to FIG. 8B, this figure illustrates a partial view of another exemplary embodiment of a plumbing system 800 having remote controlled valves 120 in addition to pressure sensors 103, pressure relief valves 803, and a heater controller 109 for controlling flow of liquid nitrogen for cooling the cryogenic chamber. This FIG. 8B is similar to the system 800 of FIG. 8A, therefore, only the differences between these two figures will be described.

According to this exemplary embodiment, the heater 110 may be coupled to a heater controller 109. The heater controller 109 may be coupled to the central controller 100 and it may be responsible for monitoring the operation of the heater 109 as described above in connection with FIG. 1D.

In addition to the heater controller 109, the system 800 of FIG. 8B (relative to FIG. 8A) may further comprise one or more plumbing pressure detectors/sensors 103. The plumbing pressure sensor 103 may be coupled to the central controller 100 and may provide pressure readings for the plumbing system 810 as described above in connection with FIG. 1D.

The system 800' of FIG. 8B may further comprise pressure relief valves 803. Exemplary pressure relief valves 803 include, but are not limited to, model REGO PRV9432F available as of this writing. Other pressure relief valves 803 are available and may be used without departing from the scope of this disclosure as understood by one ordinary skill in the art. Each pressure relief valve 803 may have a predetermined maximum pressure value which is the pressure threshold at which the relief valve will "open" to alleviate excess pressure in the plumbing system 810.

The predetermined maximum pressure value used in plumbing system 810 may comprise a value that falls between about 35.0 psi and about 50.0 psi. According to one exemplary embodiment, a first pressure relief valve 803 may have a maximum pressure value of about 35.0 psi while a second pressure relief valve 803 used in the same plumbing system may have a maximum pressure value of about 50.0 psi.

Figure 9:
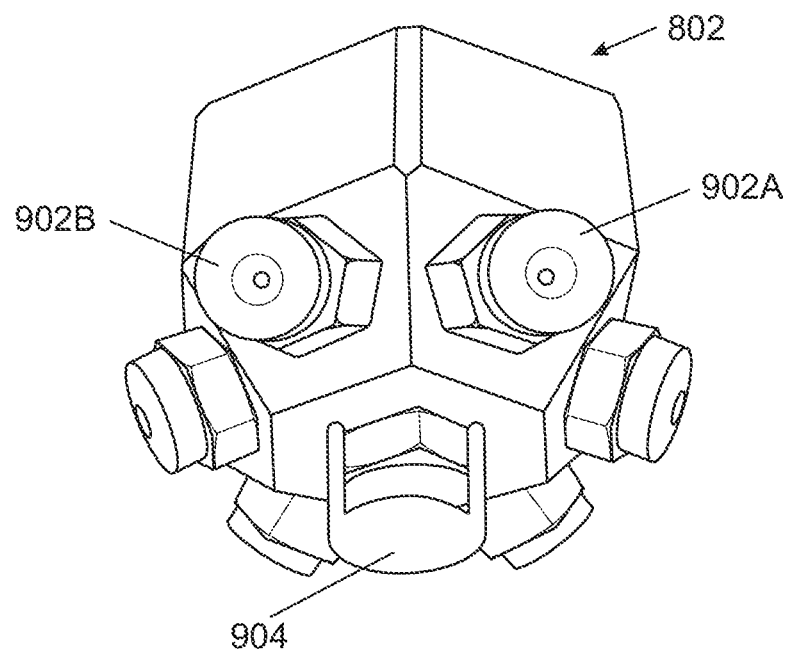
FIG. 9 illustrates a view of an exemplary nozzle used in the cryogenic chamber for directing flow of gaseous nitrogen into the cryogenic chamber for cooling the cryogenic chamber.
Figure 13:
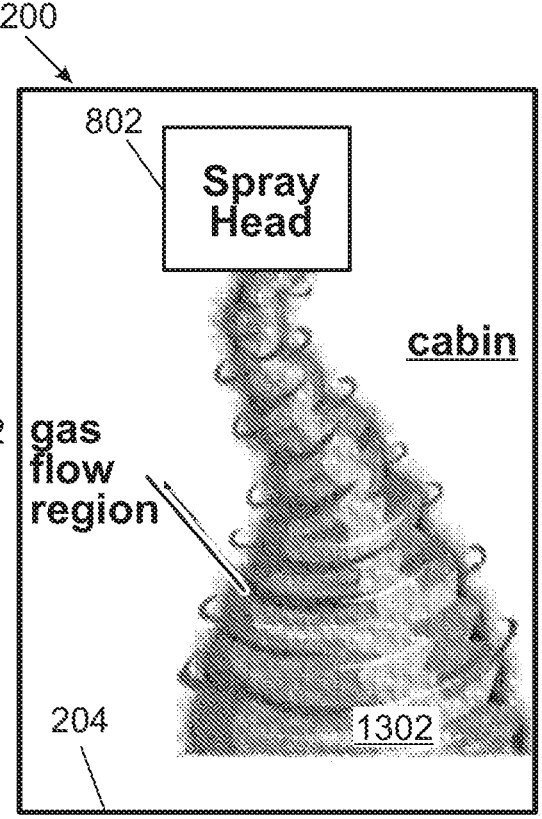
FIG. 13 illustrates an exemplary desired gas flow for the cryogenic gas (i.e. nitrogen) produced by primary nozzle of the chamber during a wholebody cryotherapy session

FIG. 9 illustrates a view of an exemplary nozzle 802 used in the cryogenic chamber 200 for directing flow of gaseous nitrogen into the cryogenic chamber 200 for cooling the cryogenic chamber 200. The nozzle 802 may comprise six jets/orifices 902A, 902B etc. for directing the gaseous nitrogen into the chamber 200. The six jets 902 may be equally distributed around the geometrical perimeter of the nozzle 802. The nozzle 802 in one exemplary embodiment has a seventh jet/orifice in the center of the nozzle 802. However, the inventors have discovered that blocking the seventh jet/orifice with a cover 904 helps product a gas flow that is unique for the chamber 200. The nozzle 802 may comprise a FOGJET brand nozzle made of brass and manufactured by SPRAYING SYSTEMS, model 3/4-7G-3, The inventors believe that that the six jets 902 with the center, seventh jet blocked by a cover 904 provide for an advantageous gas flow within the chamber 200 as illustrated in FIG. 13 and described below. The nozzle may be made from metal, and particularly, brass. However, other materials are possible and are included within the scope of this disclosure. Other materials include, but are not limited to, plastics, ceramics, and other similar materials.

Figure 10:
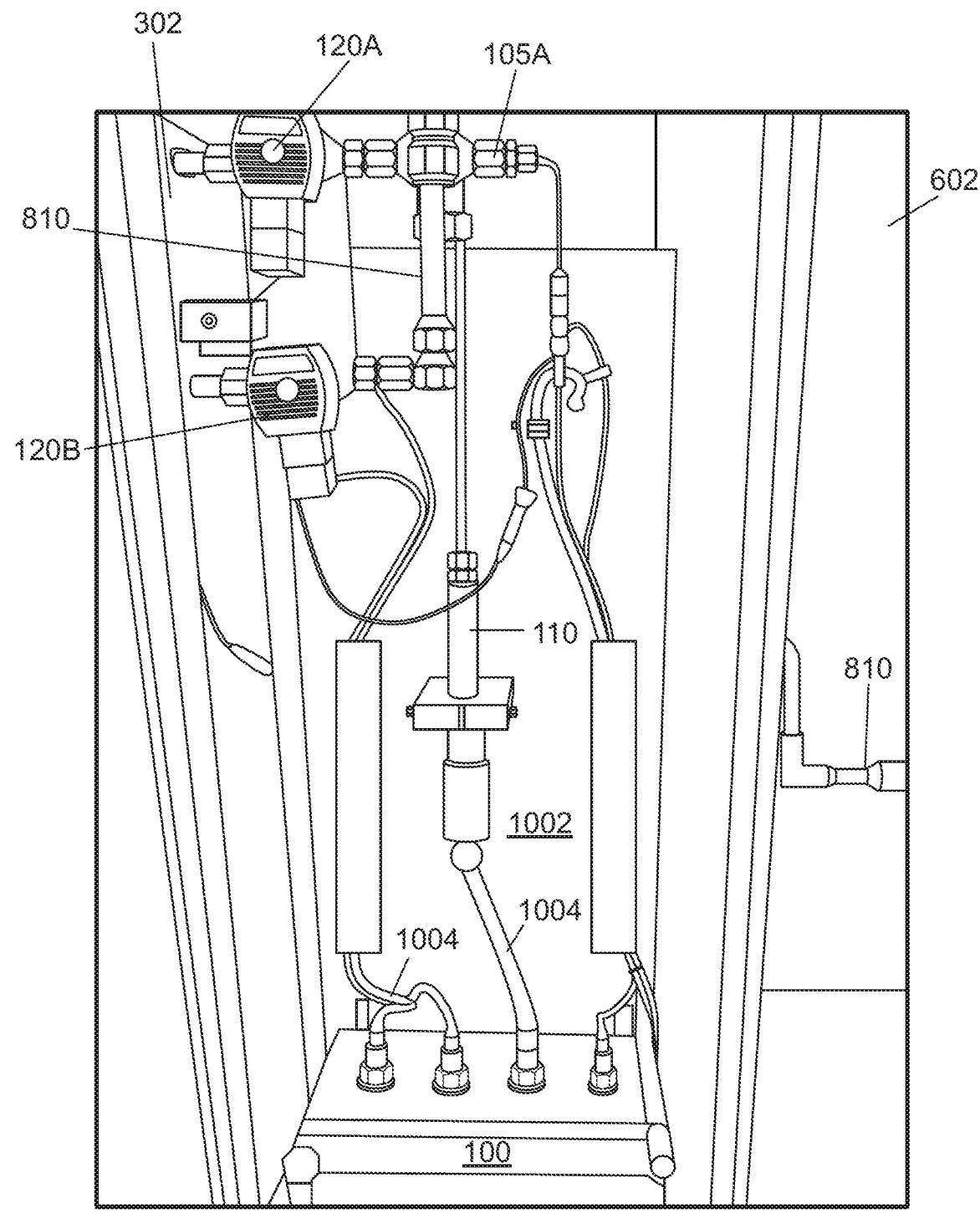
FIG. 10 illustrates an exemplary embodiment of the plumbing system of FIG. 8A in addition to the heater and temperature sensor which may be housed within the back box of FIGS. 6-7.

FIG. 10 illustrates an exemplary embodiment of the plumbing system 800 of FIG. 8 in addition to the heater 110 and temperature sensor 105A which may be housed within the back box 602 of FIGS. 6-7. The heater 110 may be coupled to a wall of the back box 602. Meanwhile, the remote control valve 120A for the cabin nozzle 802 (not visible) and the remote control valve 120B for the pre-cool nozzles 804A, 804B (not visible) and their conduits 810 are coupled to an upper region of a panel 302 that is part chamber 200.

The central controller 100 may be positioned within a lower portion of the back box 602. The central controller 100 may be coupled to the remote controlled valves 120A, 120B, temperature sensor 105A, and heater 110 by signal lines 1004. According to one exemplary embodiment, the signal lines 1004 may comprise electrical wires. Other signal lines besides electrical wires may be used. Other signal lines may include fiber optic cables. In other exemplary embodiments, the central controller 100 may be coupled to its slave components in a wireless manner by using radio-frequency (RF) units having antennas. Various combinations of how the central controller 100 may communicate with its slave components (i.e. wired and wirelessly) are possible and are included within the scope of this disclosure.

Figure 11:
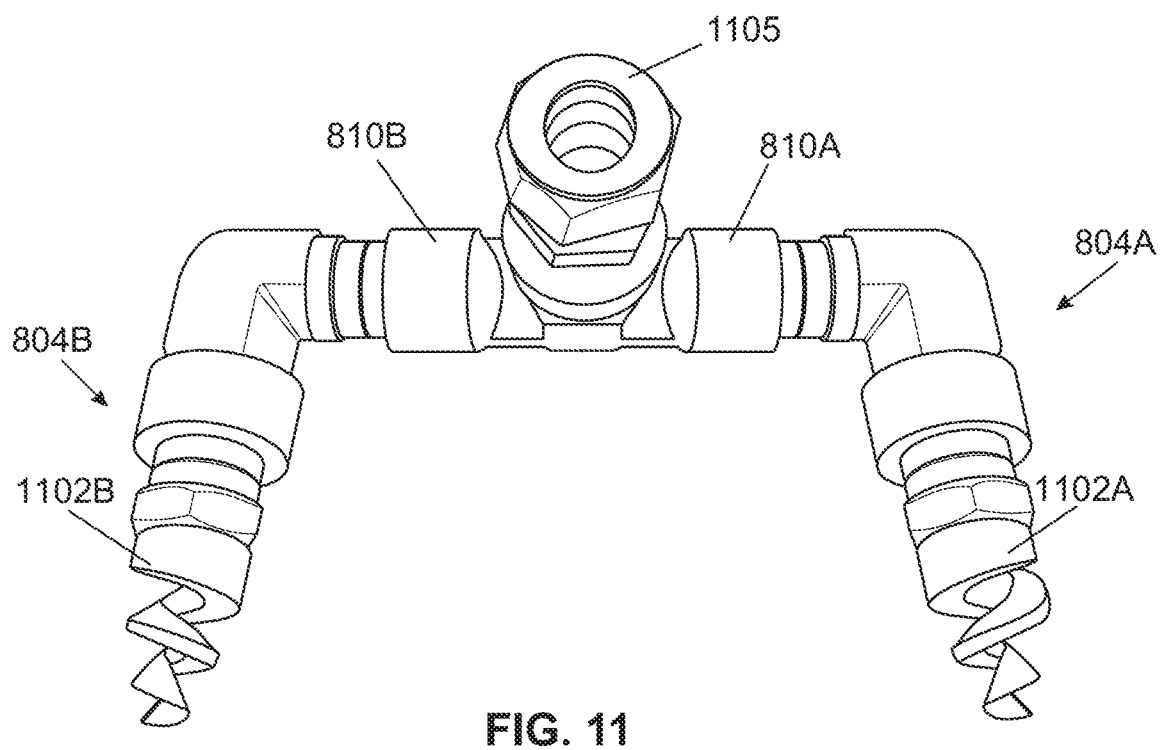
FIG. 11 illustrates two exemplary nozzles used in the cryogenic chamber for directing flow of gaseous nitrogen into the cryogenic chamber for pre-cooling the cryogenic chamber prior to a whole-body cryotherapy session.

FIG. 11 illustrates two exemplary nozzles 804A, 804B used in the cryogenic chamber 200 for directing flow of gaseous nitrogen into the cryogenic chamber 200 for pre-cooling the cryogenic chamber 200 prior to a whole-body cryotherapy session. As noted previously, the Pre-Cool stage addresses the ambient temperature of the chamber 200 before the cryogenic gas (i.e. nitrogen gas) is introduced into the chamber 200. With the Pre-Cool stage, the initial ambient temperature of the internal volume 207 defined by the chamber 200 is usually lowered. Before the air within the chamber 200 may be brought down to the desired temperature, a heat transfer will need to take place by having the cryogenic gas (i.e. nitrogen gas) remove heat from the internal volume 207. The desired pre-cool stage temperature is usually about −14.0 degrees F.

According to one exemplary embodiment, pre-cool nozzles 804A may be coupled to a central coupler/connector 1105 by its respective conduit 810A, 810B. Each conduit 810 of this embodiment may comprise an "elbow" or right angled joint such that each pre-cool nozzle 804 is coupled to a respective joint. Each pre-cool nozzle 804 may comprise a region 1102 having the geometry of a spiral. The pre-cool nozzles 804 may be manufactured by BETE, and have a model number 1/2TF24FCN.

Figure 12:
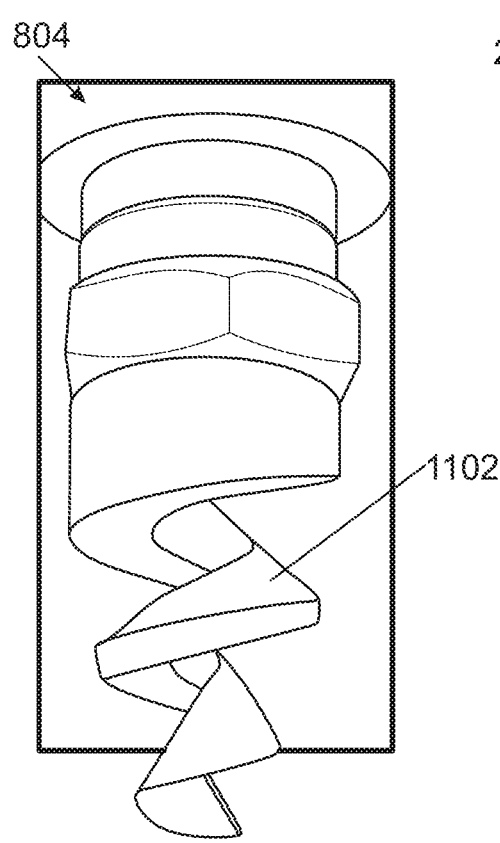
FIG. 12 illustrates a close-up view of one of the pre-cool nozzles illustrated in FIG. 11.

FIG. 12 illustrates a close-up view of one of the pre-cool nozzles 804 illustrated in FIG. 11. This figure highlights the region 1102 of each pre-cool nozzle 804 which has a spiral geometry. The pre-cool nozzles 804 provide for a cone-shaped, circular/spiral dispersion flow/distribution of the cryogenic gas as it exits each nozzle 804. The orientation of each pre-cool nozzle 804 relative to its conduit 810 is such that the flow of the cryogenic gas exiting each nozzle 804 is directed in a downward direction, flowing from cover 210 towards the base 204 and/or risers 215 (if used) of the chamber 200. The geometry of each pre-cool nozzle 804 typically limit a flare of the gas distribution to about 90.0 degrees. The ninety-degree dispersion cone of gas from nozzles 804 will limit the side-to-side dispersion of cryogenic gas and direct more of the cryogenic gas downward into the chamber 200.

FIG. 13 illustrates an exemplary desired gas flow for the cryogenic gas (i.e. nitrogen) produced by primary nozzle 802 of the chamber 200 during a wholebody cryotherapy session. The primary nozzle 802 having its six active jets 902 may produce a rotating flow for the cryogenic gas 1302 as it flows within the chamber 200.

The rotating flow of gas 1302 as illustrated in FIG. 13 may have a narrow cross-section near the nozzle 802 and it then may spread or fan out such that the rotating flow 1302 has a much larger cross-section near the base 204 of the chamber 200 which may have the risers 215 (see FIGS. 1B-1C). The inventors have discovered that this geometry, that looks like an inverse-tornado, for the gas flow 1302 produced by the primary nozzle 802 illustrated in FIG. 9 for a wholebody cryotherapy session cools the chamber 200 fairly rapidly and efficiently.

It is noted that the pre-cool nozzles 804 are not active or emitting any cryogenic gasses during a wholebody cryotherapy session. However, the primary nozzle 802 may emit cryogenic gasses when the pre-cool nozzles 804 are dispensing cryogenic gasses for pre-cooling the chamber 200, prior to a wholebody cryotherapy session. In other words, all three nozzles 802, 804A, 804B may emit cryogenic gasses during a pre-cool stage. Usually, it is recommended that a subject not be present when the chamber 200 is being pre-cooled by all three-nozzles 802, 804A, 804B. But a subject may be present when only the primary nozzle 802 is active/ON during a wholebody cryotherapy session.

When the remote control valve 120B is opened by the central controller 100 for sending cryogenic gas to the the pre-cool nozzles 804, then the remote control valve 120A for the primary nozzle 802 may also be opened by the central controller 100. And similarly, when the remote control valve 120A is open by the central controller 100 for sending cryogenic gas to the primary nozzle 802, then the remote control valve 120B for the pre-cool nozzles 804 may be closed by the central controller 100.

Figure 14:
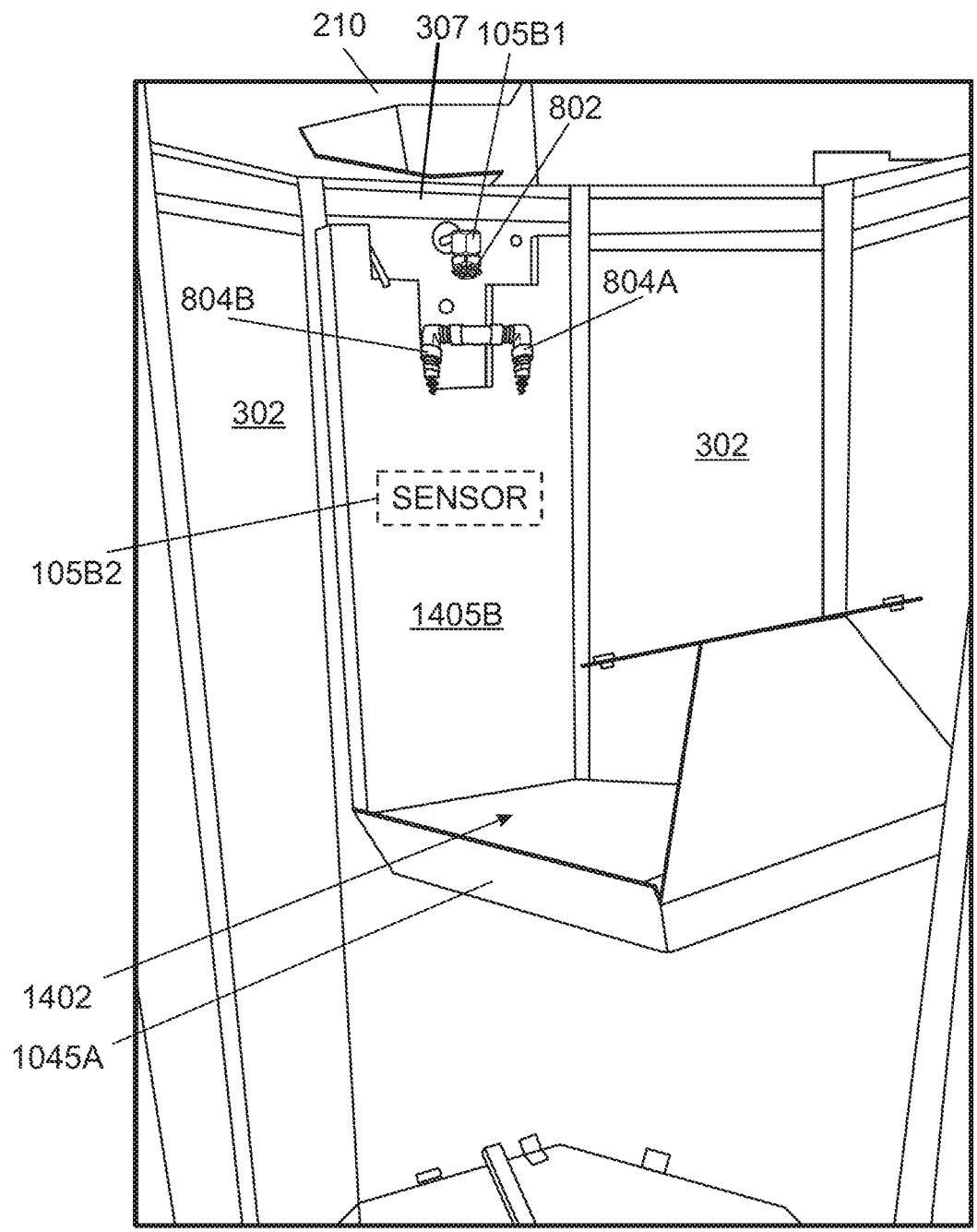
FIG. 14 illustrates one exemplary embodiment for the placement of the three nozzles of FIGS. 9, 11, and 12 within the cryogenic chamber of FIG. 1.

FIG. 14 illustrates one exemplary embodiment for placement of the three nozzles 802, 804A, 804B of FIGS. 9, 11, and 12 within the cryogenic chamber 200 of FIG. 1. The primary nozzle 802 for cooling the cryogenic chamber 200 during a wholebody cryotherapy session is positioned near an upper region of the wall 307 that is part of the back box 602 (not visible in this figure). The primary nozzle 802 is usually positioned very close to the top closable cover 210 as illustrated in FIG. 14.

The pre-cool dual nozzles 804A, 804B are positioned just below the primary nozzle 802. The positioning of the pre-cool dual nozzles 804A, 804B relative to the primary nozzle 802 is also illustrated in FIG. 8 that highlights features of the plumbing system 800 described above. As noted above, a distance D between the cap 904 of the primary nozzle 802 and the conduit 810 that connects the pre-cool nozzles 804A, 804B together is usually between about 6.0 to about 12.0 inches. See also FIG. 8.

The wall 307 for the back box 602 that is exposed in chamber 200 is usually made of a metal material as noted above and it is positioned between two wall panels 302. As noted previously, the central controller 100 usually measures temperature of the cryogenic chamber 200 at two locations using two temperature sensors 105B1, 105B2.

The first temperature sensor 105B1 may be positioned on or adjacent to the primary nozzle 802. The second temperature sensor 105B2 may be positioned along the wall 307 and positioned at a distance down from the closeable cover 210 between about 20.0 and 28.0 inches, and preferably at a distance of about 24.0 inches. Other locations for the two cabin temperature sensors 105B1, 105B2 and are included within the scope of this disclosure. Further, additional or fewer temperature sensors 105B1, 105B2 may be employed without departing from the scope of this disclosure. In FIG. 14, the second temperature sensor 105B2 has been illustrated with a functional box highlighted with dashed lines since it is located behind a stationary baffle wall 1405B described below.

A baffling system 1402 may be positioned around the three nozzles 802, 804A, 804B as illustrated in FIG. 14. The baffling system 1402 may comprise a movable wall 1405A and a stationary wall 1405A. The movable wall 1405A may be coupled to the stationary wall 1405A by a hinge (not visible) located at a lower section of the two walls 1405A, 1405B. In FIG. 14, the baffling system 1402 is shown with the first movable wall 1402 in an "opened" state such that the three nozzles 802, 804A, 804B are exposed and can be serviced as needed.

Each baffle wall 1405 is usually made from aluminum material formed and machined into a baffle panel. Each wall 1405 may be covered with material such as foam covered with anti-microbial and anti-bacterial fabric.

Figure 15:
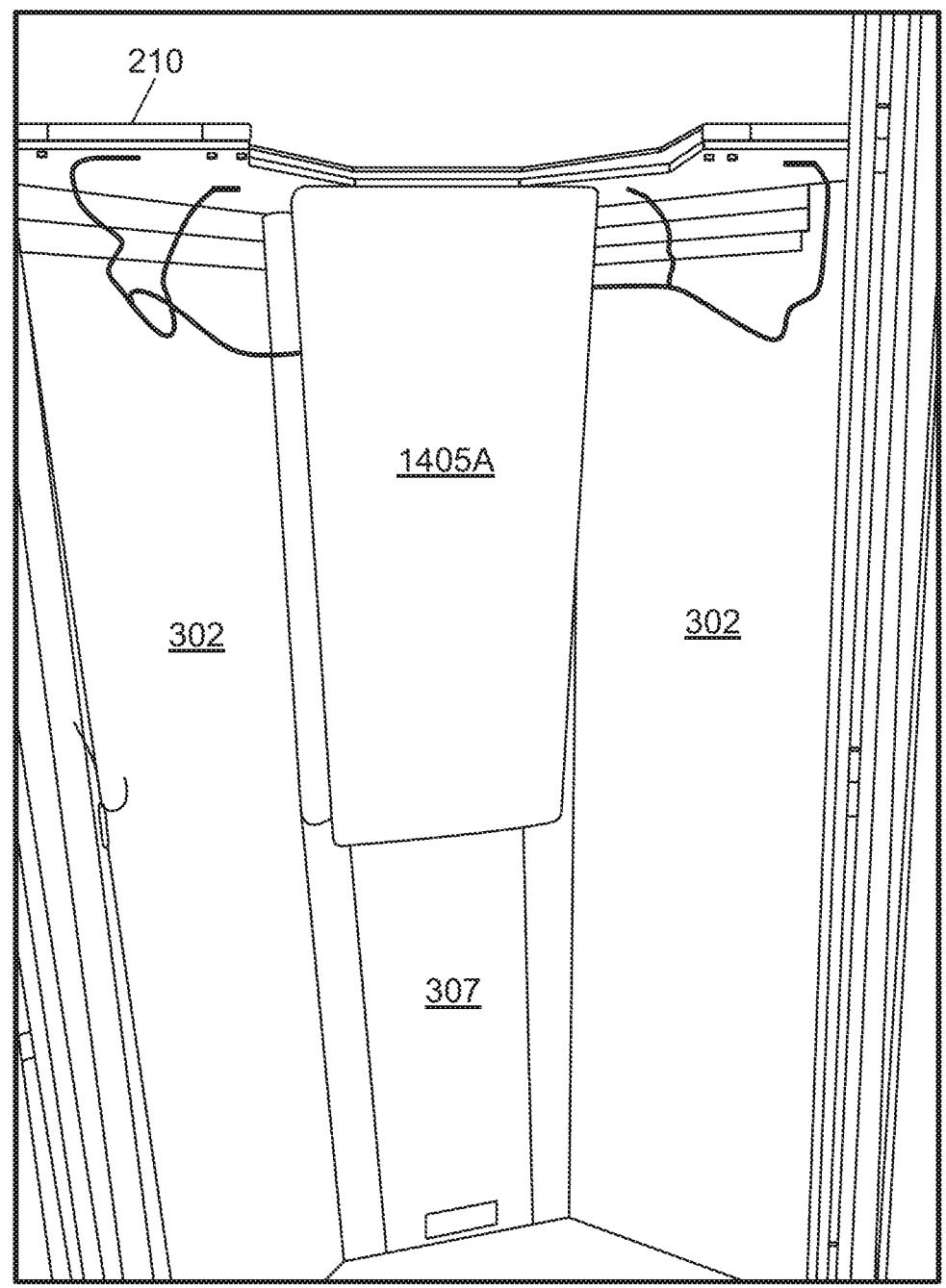
FIG. 15 illustrates a baffling system of FIG. 14 in a closed state such that the three nozzles are positioned within the walls of the baffling system.

Referring now to FIG. 15, this figure illustrates the baffling system 1402 of FIG. 14 in a closed state such that the three nozzles 802, 804A, 804B (not visible in FIG. 15 but see FIG. 14) are positioned within the two walls 1405A, 1405B of the baffling system 1402. The walls 1405 of the baffling system 1402 may protect the three nozzles 802, 804A, 804B from direct physical contact of a human subject during a wholebody cryotherapy session. The walls 1405A, 1405B have a geometry/shape and size which corresponds with metal wall 307 and wall panels 302 such that the baffling system 1402 looks very similar to wall 307 and panels 302, especially when the baffling system 1402 is in closed state which sandwiches the three nozzles 802, 804A, 804B between the two walls 1405A, 1405B.

Figure 16A:
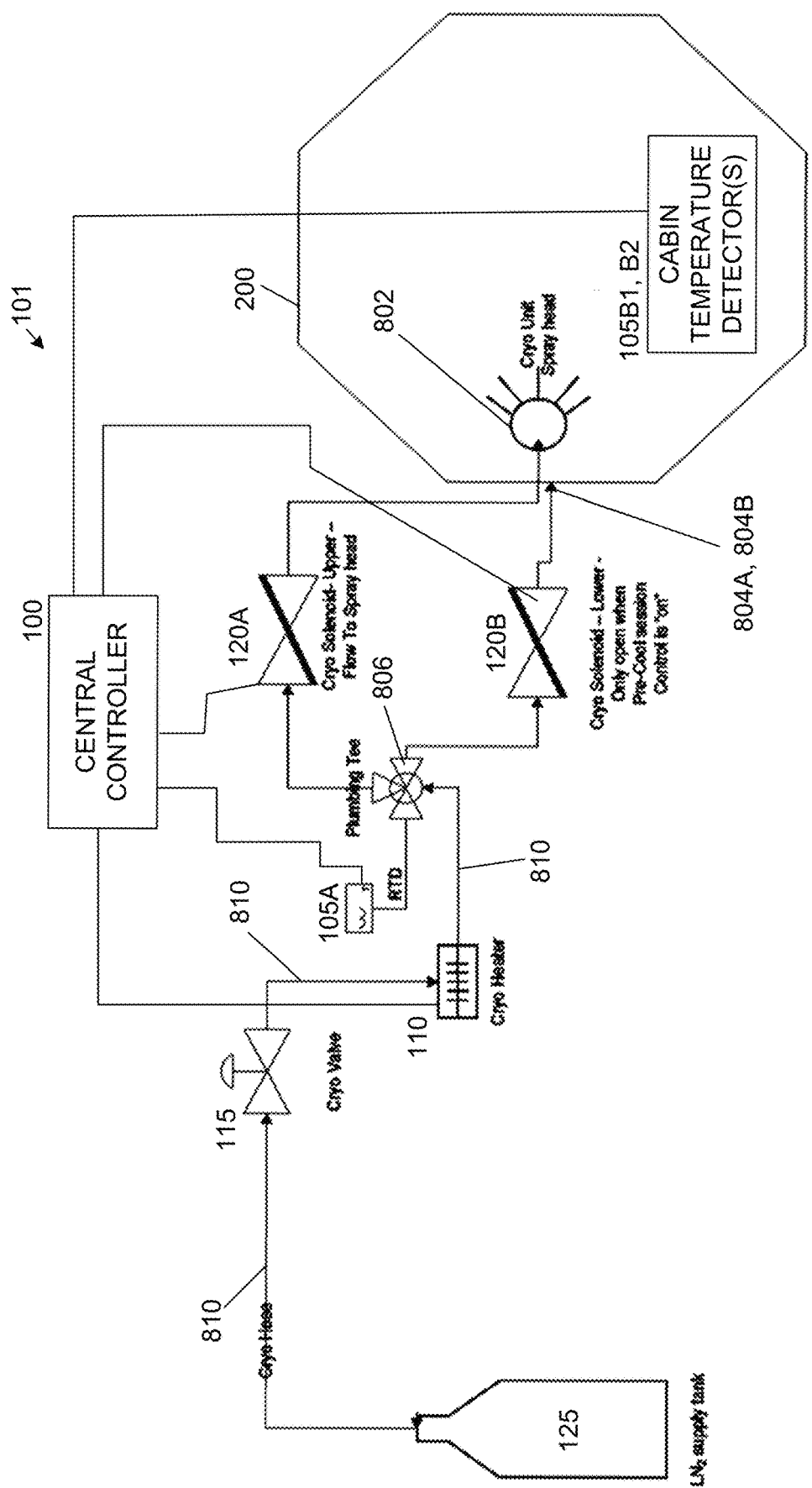
FIG. 16A illustrates one exemplary embodiment of a cryogenic fluid flow diagram for the cryogenic cooling system that is controlled by the central electronic controller of FIG. 1D.

FIG. 16A illustrates one exemplary embodiment of a cryogenic fluid flow diagram for the cryogenic cooling system 100 that is controlled by the central electronic controller 100 of FIG. 1D. As noted previously, the central controller 100 may be coupled to the cryofluid heater 110, temperature sensors 105, and remote controlled valves 120. Compared to the exemplary embodiment illustrated in FIG. 16B (described in detail below), this exemplary embodiment of FIG. 16A does not have one or more pressure sensors 103, one or more pressure relief valves 803, and a heater controller 109.

The cryogenic fluid, that usually comprises liquid nitrogen, is stored in a cryogenic fluid supply 125. The cryogenic fluid supply 125 usually comprises a steel, pressurized container in which the cryogenic liquid is stored under pressure. The cryogenic fluid supply 125 is coupled to a cryogenic fluid supply valve 115 by a conduit 810. As noted previously, the cryogenic fluid supply valve 115 may comprise hardware which is manually operated. However, the manually driven cryogenic fluid supply valve 115 could be substituted with a remote controlled valve 120 that is controlled by the central controller 100 as understood by one of ordinary skill in the art.

Another conduit section 810 couples the cryogenic fluid supply valve 115 to the cryogenic fluid heater 110. The cryogenic fluid heater 110 is coupled to and is under control by the central controller 100. The central controller 100 activates the fluid heater 110 if the temperature of the cryogenic fluid is not at a predetermined temperature when exiting one or more of the cabin spray heads/nozzles 802 during a cryotherapy session.

The predetermined temperature is one that is about at or above −192.0 degrees Celsius. If the temperature of the cryogenic fluid exiting a cabin spray head is below this predetermined temperature (meaning that the cryogenic fluid is too cold for a cryogenic therapy session), then the central controller 100 may activate the remote-controlled cryogenic heater 110 in order to warm or heat the cryogenic fluid to reach the predetermined temperature as measured at the primary nozzle 802 with first chamber temperature sensor 105B1 (see FIG. 14) and/or with second chamber temperature sensor 105B2 (see FIG. 14).

The cryoheater 110 is coupled to the plumbing-tee section 806 by another conduit 810. A plumbing temperature sensor 105A measures temperature of the cryogenic fluid at the plumbing-tee section 806. The plumbing-tee section 806 is the junction at in which two fluid paths are created/connected: a first fluid path flows to a first remote control valve 120A which is coupled to the primary nozzle 802; a second fluid path flows to the second remote control valve 120B which is coupled to the two pre-cool nozzles 804A, 804B.

As noted previously, the central controller 100 will open remote controlled valve 120B which is coupled to the pre-cool dual nozzles 804A, 804B, prior to a wholebody cryotherapy session in order to remove ambient heat from the cryogenic chamber 200. During the pre-cool stage/cycle, the central controller may also open remote controlled valve 120A coupled to the primary nozzle 802 so that all three nozzles 802, 804A, 804B are active and are cooling the chamber 200 during a pre-cool stage. As noted previously, it is recommended that a subject not be present and that the chamber 200 is unoccupied during a pre-cool stage.

When the central controller 100 detects that the cryogenic chamber 200 has reached the predetermined temperature set for the pre-cool stage by readings sent from the two temperature sensors 105B1, 105B2 (see FIG. 14) for the chamber 200, then the central controller 100 will close remote controlled valve 120B such that cryogenic gas no longer flows through pre-cool nozzles 804A, 804B.

Next, if the central controller 100 detects that the chamber 200 is ready for a cryotherapy session (via input devices like the touch-screen display 147—see FIG. 1A), then the central controller 100 will open the remote controlled valve 120A coupled to the primary nozzle 802. Cryogenic gas will then flow through primary nozzle 802 for cooling the cryogenic chamber 200 for a wholebody cryotherapy session.

During a whole body cryotherapy session, the central controller 100 continuously monitors temperature detectors 105A (for the plumbing system), 105B (for the chamber 200), to insure that efficient and adequate cooling occurs within the cryogenic chamber 200. As the controller 100 detects temperature variances with sensors 105, it can turn/cycle the cryo-heater 110 on and/or off to address these variances in temperature.

Figure 16B:
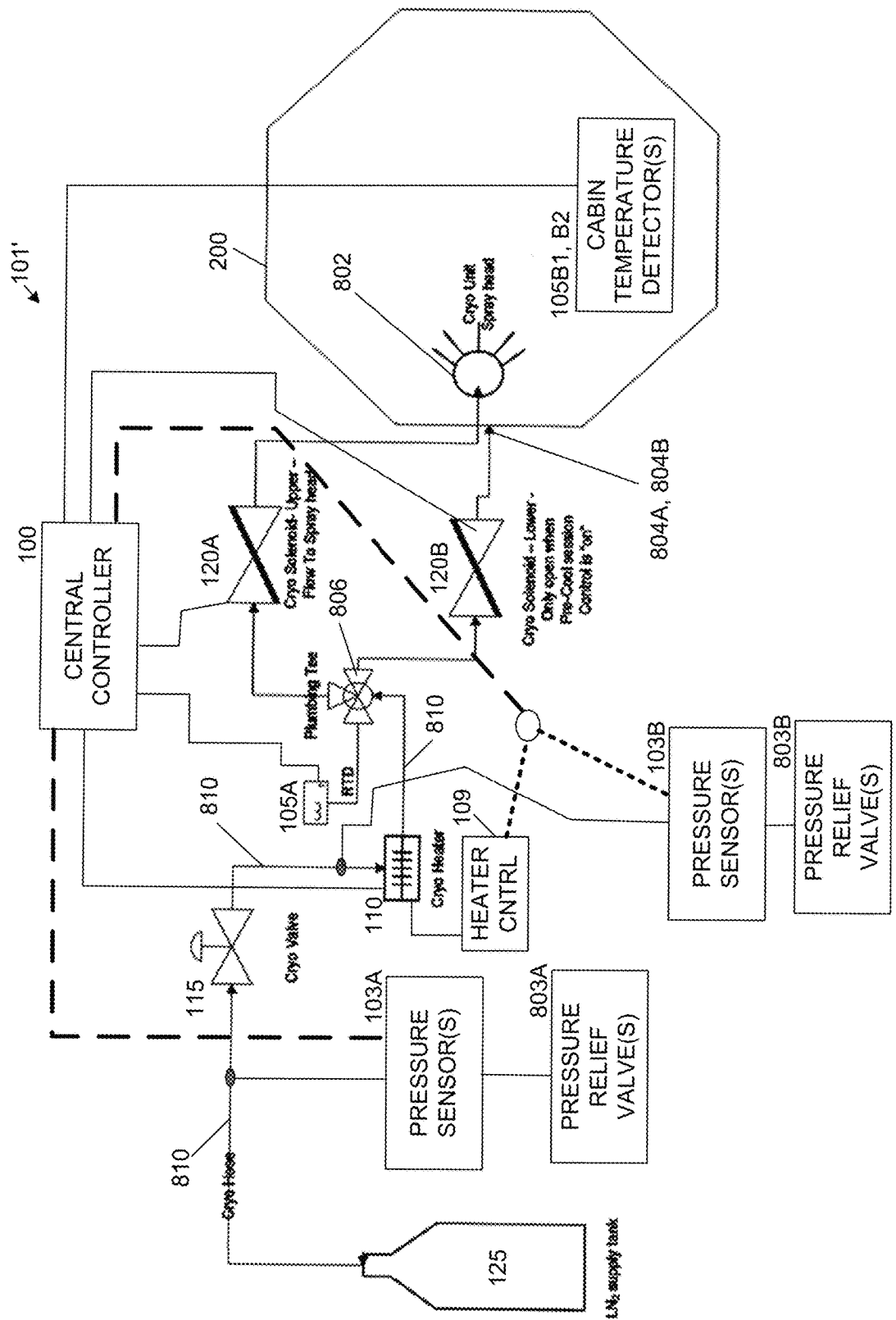
FIG. 16B illustrates another exemplary embodiment of a cryogenic fluid flow diagram for the cryogenic cooling system which has pressure sensors and a heater controller that are controlled by the central electronic controller of FIG. 1D.

FIG. 16B illustrates another exemplary embodiment of a cryogenic fluid flow diagram for the cryogenic cooling system 100' (prime) which has pressure sensors and a heater controller that are controlled by the central electronic controller of FIG. 1D. Compared to the exemplary embodiment illustrated in FIG. 16A (described in detail above), this exemplary embodiment of FIG. 16A does include one or more pressure sensors 103, one or more pressure relief valves 803, and a heater controller 109.

FIG. 16B is very similar to the exemplary embodiment illustrated in FIG. 16A, therefore, only the differences between these exemplary embodiments will be described below. As noted previously, the pressure sensors/detectors 103 may comprise a pressure transducer. Exemplary transducers may include, but are not limited to, transducers manufactured by Turk, model number PT100PSIG-13-LI3-H1131, as of this writing. Each plumbing pressure sensor 103 may monitor the pressure in the plumbing 810 and may send pressure information to the central controller 100.

As noted previously, the pressure relief valves 803 may include, but are not limited to, model REGO PRV9432F available as of this writing. Other pressure relief valves 803 are available and may be used without departing from the scope of this disclosure as understood by one ordinary skill in the art. Each pressure relief valve 803 may have a predetermined maximum pressure value which is the pressure threshold at which the relief valve will "open"/activate to alleviate excess pressure in the plumbing system 810.

The heater controller 109 may comprise a overheat/high temperature safety circuit built into the heater 110. When the temperature of the heater 110 exceeds about 190.0 degrees F., the heater controller 109 may shut down (turn off electrical power to) the heater 110. The heater controller 109 may also comprise a circuit/hardware that may alert the central controller 100 if the heater 109 is not functioning properly. According to one exemplary embodiment, the heater controller 109 may comprise a monitoring relay that may be tapped into a 120 VAC wire past a main heater relay circuit.

When the monitoring relay of the heater controller 109 "sees"/determines that a voltage threshold had been met, it may close the circuit preventing power to the heater 110 and then transmit a message to the central controller 100. If the heater 110 is supposed to be on and the central controller 100 does not receive a message from the heater controller 109 (where the message may comprise a 24 VDC signal), the central controller 100 may shut down all its slaves/devices and it may display a heater failure message that is illustrated in FIG. 18E described in further detail below.

Figure 17A:
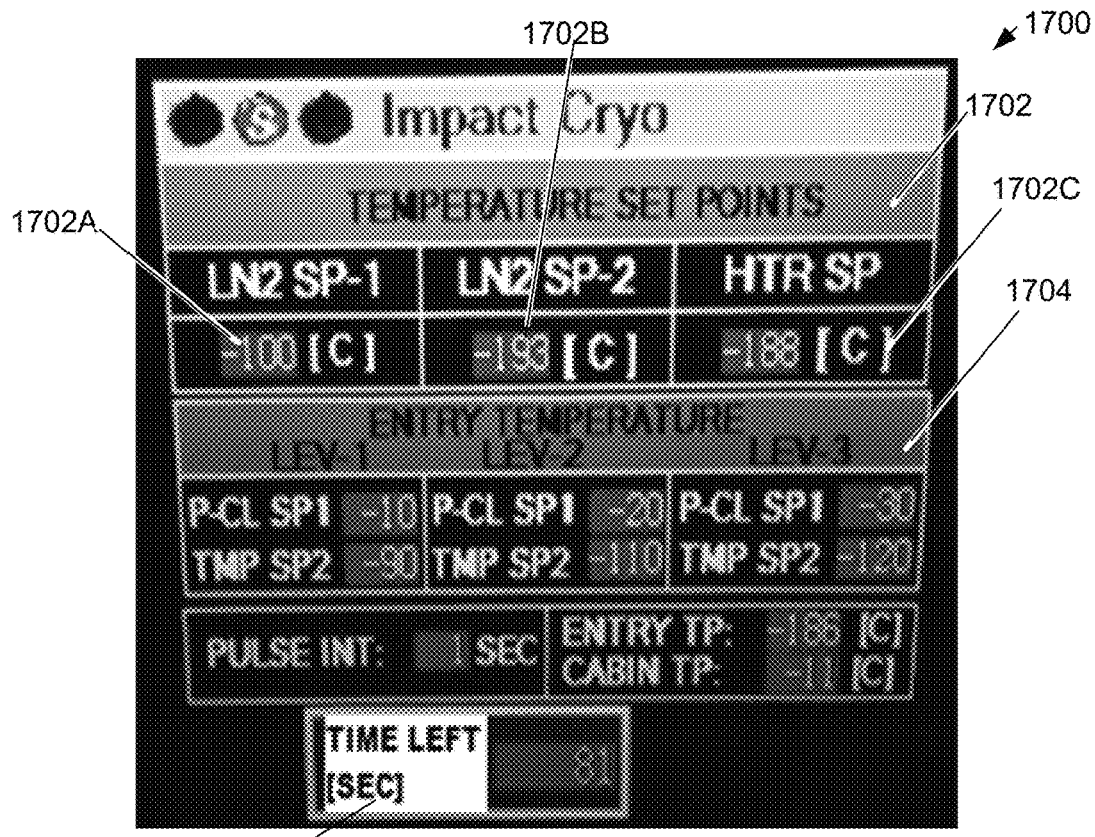
FIG. 17A illustrates one exemplary embodiment of a screen shot for the display device generated by the electronic central controller for receiving input on the temperature set points used for the cryogenic chamber of FIG. 1.

Referring now to FIG. 17A, this figure illustrates one exemplary embodiment of a screen shot 1700 for the display device 147 generated by the electronic central controller 100 for receiving input on the temperature set points 1702 used for the cryogenic chamber 200 of FIG. 1. The operator of the cryothearpy system 101 may input a first set of temperature set points 1702 using the touch-screen display device 147. The first temperature set point 1702A is for temperature within the chamber 200, which may have default setting of about minus (–)100.0 degrees Celsius.

The second temperature set point 1702B is the temperature set point for the temperature sensor 105A designed to monitor the temperature of the cryogenic gas at the plumbing tee section 806 (See FIG. 8), which may have a default setting of about minus (–)193.0 degrees Celsius. The third set point 1702C is a heater temperature set point that assigns a temperature for activating the heater when the the cryogenic fluid as it exits the heater 110 reaches this temperature. This third set point 1702C may have a default setting of about minus (–)189.0 degrees Celsius.

Usually, the cryogenic fluid from the fluid supply 125, which usually is in the form of a liquid at the supply 125, turns into a cryogenic gas before it exits anyone of the three nozzles 802, 804A, 804B. Usually, the cryogenic liquid turns into gas at an exit portion of the heater 110 or just prior to the tee-section 806 of plumbing system 800. See FIG. 8. The heater 110 and friction within the plumbing system 800 transform any liquid form of the cryogenic fluid into a cryogenic gas that exits the three nozzles 802, 804A, 804B into the chamber 200.

A second set of temperature set points 1704 may be provided by an operator using the touch-screen display device 147. The second set of temperature set points 1704 may include temperatures that may be set for three different levels associated with a pre-cooling stage and wholebody cryotherapy sessions. That is, an operator may set/input the temperature for each pre-cooling stage that takes place before each cryotherapy session using the touch-screen display device 147. The cryotherapy system 101 may provide for at least three different levels, each having a unique temperature, for pre-cooling stages as well as wholebody cryotherapy sessions. While only three levels are illustrated, one of ordinary skill in the art recognizes that fewer or additional levels could be provided without departing from the scope of this disclosure.

The operator indicate to the central controller 100 at what time the central controller 100 should start displaying the time remaining or left for a particular cryotherapy session with time-left/remaining adjustment field 1706.

Figure 17B:
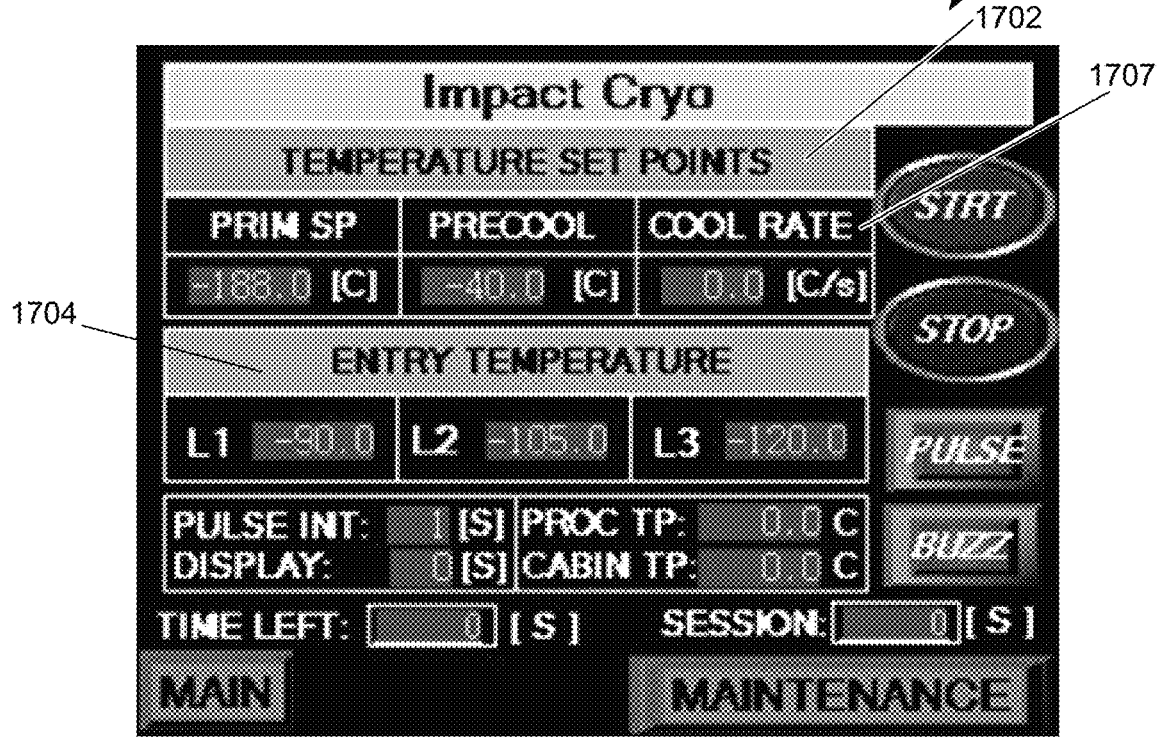
FIG. 17B illustrates another exemplary embodiment of a screen shot for the display device generated by the electronic central controller for receiving input on the temperature set points used for the cryogenic chamber of FIG. 1.

Referring now to FIG. 17B, this figure illustrates another exemplary embodiment of a screen shot 1700 for the display device 147 generated by the electronic central controller 100 for receiving input on the temperature set points used for the cryogenic chamber of FIG. 1. This exemplary embodiment illustrated in FIG. 17B is similar to the one illustrated in FIG. 17A. Therefore, only the differences between these two embodiments will be described below.

According to this exemplary embodiment of FIG. 17B, a cooling rate 1707 may be set/adjusted by the operator of the system 101. The cooling rate 1707 may insure that the temperature in the Cryo Sauna does not cool too quickly. The rate of cool is typically set to about –1.0 degree Celsius per second. However, other rates higher or lower than this setting may be selected as desired and as understood by one of ordinary skill in the art. This cooling rate 1707 is usually only active when a Cryo-session is active and will enable the heater controller 109 to turn on the heater 110 if the cooling rate exceeds the rate of cooling setting.

FIG. 18A illustrates one exemplary embodiment of a screen shot 1800 for the display device 147 generated by the electronic central controller 100 for receiving input for the options that may be selected for a cyrotherapy session. This screen 1800 may be displayed when the cryotherapy system 101 is ready to receive a subject within chamber 200 for initiating a cryotherapy session.

In this exemplary embodiment, the operator for the system 101 may select from one of the three cryotherapy session time limits 1802A, 1802B, 1802C. These time limits may be expressed in minutes, but other time increments may be used without departing from the scope of this disclosure. In the exemplary embodiment illustrated, the first level 1802A has a duration of one minute while the second level 1802B has a duration of two minutes while the third level has a duration of three minutes.

The operator may adjust the durations of these levels such they each may be longer or shorter than what is illustrated. Also, other time increments may be used without departing from this disclosure: instead of minutes, the unit of seconds could be used. Field 1810 of the screen 1800 may also display the current temperature of the cryogenic chamber 200.

Once a level for a cryotherapy session is selected (either the first, second, or third level), then operator may select/activate the pre-cool stage with the pre-cool on-screen button 1804. The operator of the system 100 may then select the start on-screen button 1806 in order to initiate the pre-cool stage for the cryogenic chamber 200. During this pre-cool stage, it is recommended that a human subject NOT occupy the internal volume 207 defined by the cryogenic chamber 200. At any point during the pre-cool stage and even during a cryotherapy session, the operator may select the stop on-screen button 1808 to stop cooling of the cryogenic chamber 200. Upon receiving the stop command, the central controller may close all valves 120 in order to stop cooling of the cryogenic chamber 200.

Referring now to FIG. 18B, this figure illustrates another exemplary embodiment of a screen shot 1800 for the display device 147 generated by the electronic central controller 100 for receiving input for the options as well as displaying a first status pressure message 1803A for a cryotherapy session. FIG. 18B is similar to FIG. 18A, therefore, only the differences between these figures will be described below.

When pressure is monitored in this "normal" range by a plumbing pressure sensor 103, the central controller 100 may allow a standard/normal cryotherapy session to be run and the central controller 100 may send a "normal" range first status pressure message 1803A as illustrated in FIG. 18B to the display device 147. The central controller 100 may also display an actual numerical value of the current pressure within the plumbing 810 with a pressure value message 1805 as illustrated in FIG. 18B. The numerical value of the current pressure may be displayed in standard units as understood by one of ordinary skill in the art.

Referring now FIG. 18C illustrates another exemplary embodiment of a screen shot 1800 for the display device 147 generated by the electronic central controller 100 in which a second status pressure message 1803B is displayed. FIG. 18C is similar to FIG. 18A & FIG. 18B, therefore, only the differences between these figures will be described below.

When central controller 100 receives an input signal from a plumbing pressure sensor 103 that is lower than the "normal operating pressure range," the central controller 100 may change the normal first pressure status message 1803A as illustrated in FIG. 18B to a low second pressure status message 1803B as illustrated in FIG. 18C.

When the low second pressure status message 1803B of FIG. 18C is displayed on the display device 147, the system will continue to operate, however, the low pressure condition may lead to an ineffective cryotherapy session. The pressure in the plumbing 810 (as illustrated in FIG. 16 described above) is required to be in a specific range of pressures to operate the cryo-chamber 200 effectively and efficiently.

FIG. 18D illustrates another exemplary embodiment of a screen shot 1800 for the display device 147 generated by the electronic central controller 100 in which an out-of-range pressure message 1803c is displayed. In the event that one of the pressure sensors 103 detects pressures that exceed about 30.0 psi, the central controller 100 displays the "out-of-range" pressure status message 1803C on the display device 147 as illustrated in FIG. 18D. The central controller 100 may then initiate a complete shutdown of the system 101 to stop the flow of the cryogenic fluid, such as, but not limited to Nitrogen, into the cryo-chamber 200.

The central controller 100 may also generate and display another status message 1803D adjacent to the out-of-range pressure message 1803C which indicates to the operator how the pressure problem detected may be resolved/fixed. In the exemplary message 1803D of FIG. 18D, the operator is instructed to check the operations manual and to adjust the dewar which includes the plumbing 810 and corresponding manual valve 115 of FIG. 8.

While the exemplary status message 1803D adjacent to the "out-of-range" pressure message 1803C illustrated in FIG. 18D addresses a "high pressure" situation, the central controller 100 may also display one or more messages if the system 101' encounters a low pressure situation in which the pressure within the plumbing 810 is below the "normal range." In such a scenario/situation, the exemplary status message 1803D may indicate a low pressure condition and instruct the operator how to resolve the low pressure condition/problem.

The shutdown process performed by the central controller 100 for a high pressure condition may be similar to the emergency stop condition described previously that may be activated by the emergency shut-off switch 505. During a shutdown process, the central controller 100 may send one or more messages to the remote controlled valves/solenoids 120 to force them to close—if they are open and the central controller may also issue an audible message such as a "beep sound" to the audio device 145 to provide an audible indication that conditions of the cryo-sauna are changing.

In addition to the first two status messages 1803C and 1803D displayed in the screen shot 1800 illustrated in FIG. 18D, the central controller 100 may generate a third message 1803E which comprises a command prompt requesting if the operator would like the system 101 to perform a complete "reset" instead of the system 101 shutting down.

If an operator within a predetermined range of time relative to when an out-of-range pressure condition is detected by the central controller 100 selects the "reset" command 1803E on display device 147, then the central controller 100 will initiate a complete system reset similar to when the system 101 is first powered on instead of completing a system shut-down. The predetermined period of time may comprise a range of minutes or seconds. For example, the range of time may comprise between about 10.0 seconds to 600.0 seconds. However, other ranges of time may be selected/chosen without departing from the scope of this disclosure as understood by one of ordinary skill in the art.

FIG. 18E illustrates another exemplary embodiment of a screen shot 1800 for the display device 147 generated by the electronic central controller 100 in which a heater failure message 1803F is displayed. If the heater 110 is supposed to be "on"/operational and the central controller 100 does not receive a message from the heater controller 109 (where the message may comprise a 24 VDC signal), the central controller 100 may shut down all its slaves/devices and it may display the heater failure message 1803F that is illustrated in FIG. 18E.

The shutdown process performed by the central controller 100 for the heater failure condition may be similar to the emergency stop condition described previously that may be activated by the emergency shut-off switch 505. During a shutdown process, the central controller 100 may send one or more messages to the remote controlled valves/solenoids 120 to force them to close—if they are open and the central controller may also issue an audible message such as a "beep sound" to the audio device 145 to provide an audible indication that conditions of the cryo-sauna are changing.

In addition to the heater failure message 1803F displayed in the screen shot 1800 illustrated in FIG. 18E, the central controller 100 (similar to FIG. 18D) may generate a reset message 1803E which comprises a command prompt requesting if the operator would like the system 101 to perform a complete "reset" instead of the system 101 shutting down for the heater failure condition.

If an operator within a predetermined range of time relative to when a heater failure condition is detected by the central controller 100 selects the "reset" command 1803E on display device 147, then the central controller 100 will initiate a complete system reset similar to when the system 101 is first powered "on" instead of completing a system shut-down. The predetermined period of time may comprise a range of minutes or seconds. For example, the range of time may comprise between about 10.0 seconds to 600.0 seconds. However, other ranges of time may be selected/chosen without departing from the scope of this disclosure as understood by one of ordinary skill in the art.

Figure 19:
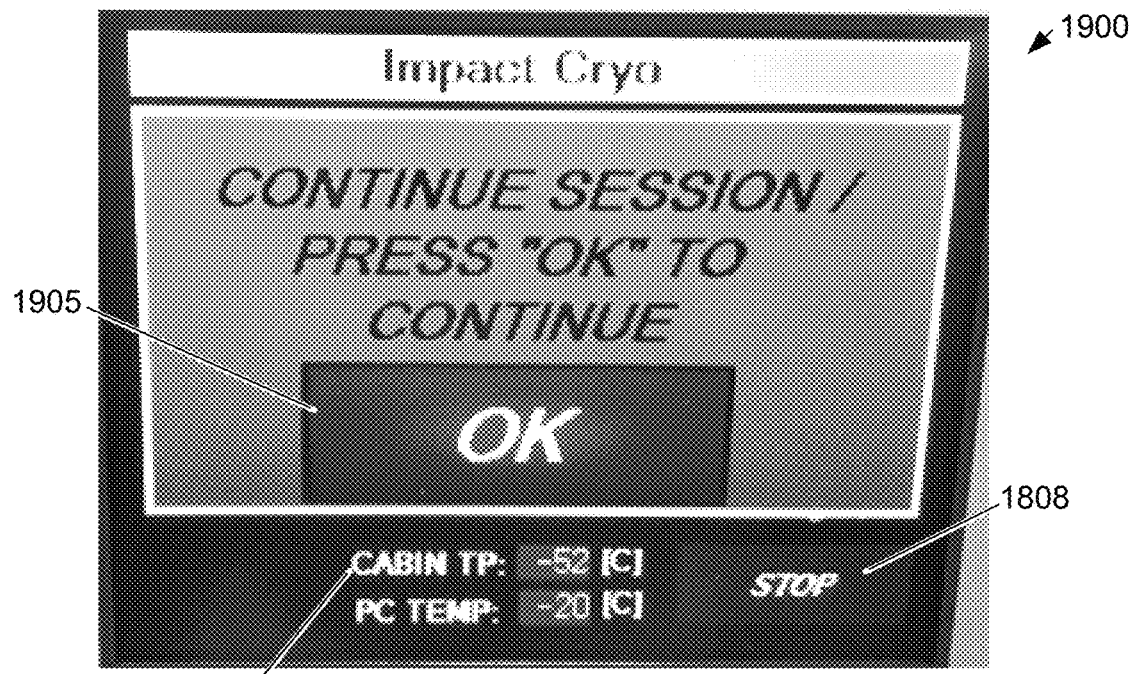
FIG. 19 illustrates one exemplary embodiment of a screen shot for the display device generated by the electronic central controller during a cryotherapy session that prompts for human input of an operator to allow a session to continue.

Referring now to FIG. 19, this figure illustrates one exemplary embodiment of a screen shot 1900 for the display device 147 generated by the electronic central controller 100 during a cryotherapy session that prompts for human input of an operator to allow a cryotherapy session to continue. According to this exemplary embodiment, the central controller 100 may generate an on-screen button 1905 that must be selected by the operator after a predetermined amount of time once a cryotherapy session is selected from the display 1800 of FIG. 18. In addition to displaying the on-screen button 1905, the central controller 100 may also produce an audible noise with an audio device 145 (see FIG. 1D). The noise may comprise an audible tone or even synthesized/machine generated speech.

The predetermined amount of time when the central controller 100 may display prompt 1905 may comprise an amount between about 2.0 seconds to about 10.0 seconds. The central controller 100 may also require this prompt 1905 be selected by a human operator on increments between about every 2.0 seconds to about 10.0 seconds. Increments of time higher or lower than this range are possible and are included within the scope of this disclosure. In this way, the central controller 100 requires frequent input from the human operator to make sure that the subject exposed in the cryogenic chamber 200 to the cryogenic temperatures is doing well. The display 1900 may also feature the current temperature 1810. At any point during a wholebody cryotherapy session, the human operator may select the stop button/function 1808 which functions as described above.

As noted previously, the display device 147 requiring input from a human operator is usually mounted and fixed on the exterior structure of the cryogenic chamber 200. However, it is envisioned that the display device 147 could be one that is part of a portable computing device such as a mobile phone or a tablet PC that can be movable and/or is portable. If a portable computing device is designed/programmed to work with the central controller 100, then a geo-fence/proximity detector may be employed such that the portable computing device which communicates with the central controller 100 must be within a radius of only a few feet (i.e. one meter or less) relative to the cryogenic chamber 200. This size of this radius is intended to be very small so that it may require the operator to have visual contact with the subject of the cryotherapy session. If the portable computing device goes beyond the small radius/radio-range, the central controller 100 may detect this "out-of-range" condition and stop the cryotherapy session within chamber 200 as appropriate.

Figure 20:
FIG. 20 illustrates one exemplary embodiment of a screen shot for the display device generated by the electronic central controller for initiating a pre-cool stage prior to a cryotherapy session.

Referring now FIG. 20 illustrates one exemplary embodiment of a screen shot 2000 for the display device 147 generated by the electronic central controller 100 for initiating a pre-cool stage prior to a cryotherapy session. The central controller 100 may generate screen 2000 when it determines from the chamber temperature sensors 105B that the temperature of the chamber 200 is too warm for a cryotherapy session to begin. The central controller 100 may determine that the pre-cool stage may take longer a few minutes, so it may generate a prompt 2005 requesting the human operator to verify that the chamber 200 is empty before the pre-cool stage is initiated.

Figure 21A:
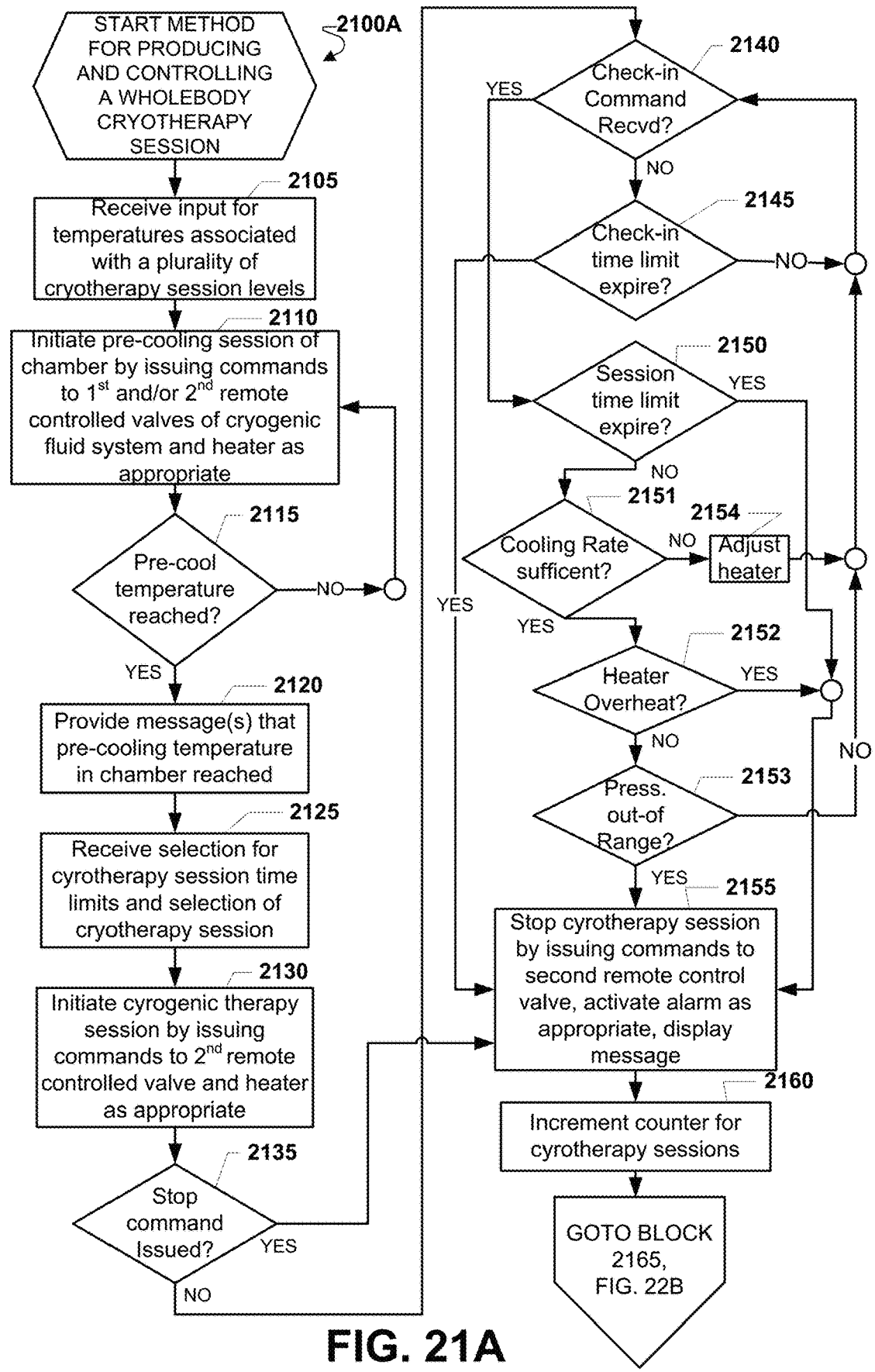
FIGS. 21A-21B are a logical flow chart illustrating one exemplary embodiment of a method for providing whole body cryotherapy.
Figure 21B:
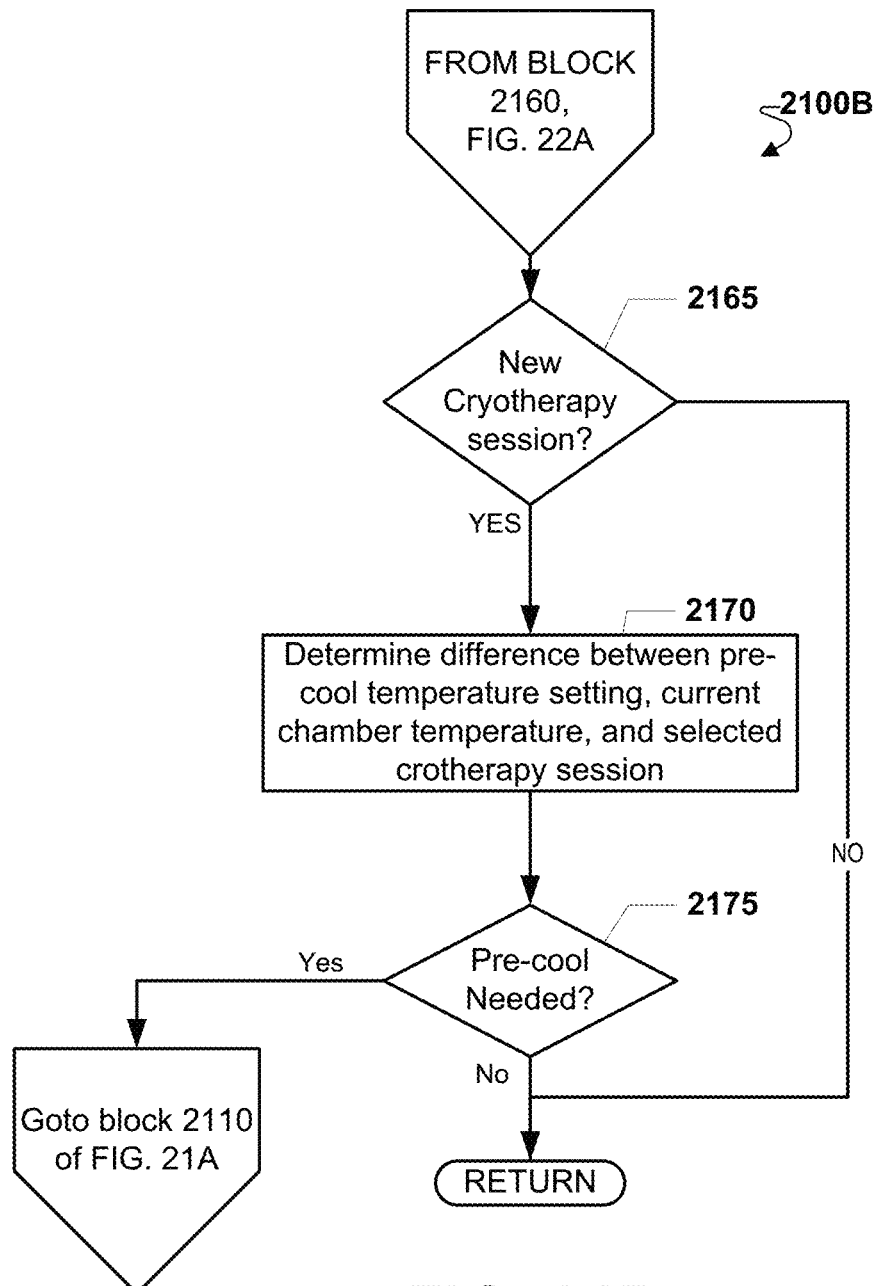

FIGS. 21A-21B are a logical flow chart illustrating one exemplary embodiment of a method 2100 for automatically producing and controlling a wholebody cryotherapy session. Block 2105 is the first step of method 2100A of FIG. 21A.

In block 2105, the central controller 100 may receive input for one or more temperatures associated with a plurality of selectable cryotherapy session levels. This block 2105 may generally correspond with FIG. 17 and/or FIG. 18 described above. As noted above, an operator for the system 101 may use a touch-screen display 147 as illustrated in FIGS. 17-18 to input/key-in desired temperatures for the cryotherapy session levels as well as temperatures for pre-cooling of the cryogenic chamber 200.

Block 2105 may also correspond to when an operator wants to initiate a cryotherapy session after inputting the baseline temperatures during the set-up phase illustrated in FIG. 17. At block 2105, the operator may select one of the three cryotherapy session levels as illustrated in FIG. 18: level one, level two, or level three. As noted above, fewer or additional cryotherapy session levels may be provided without departing from the scope of this disclosure.

In block 2110, the central controller of FIG. 1D may initiate a pre-cooling session for the cryogenic chamber 200 by issuing commands to the first and/or second remote controlled valves 120 which control the flow of the cryogenic fluid from the fluid supply 125 through the plumbing system 800 (See FIG. 8) and through the pre-cooling nozzles 804 as cryogenic gas. During this stage/block 2110, the central controller 100 may monitor temperature sensors 105. Specifically, the central controller 100 may monitor the temperature sensors 105A of the plumbing system 800 as well as the temperature sensors 105B of the chamber 200. Depending on the temperatures detected with the sensors 105 and processed by the central controller 100, the central controller 100 may send commands to the cryo-heater 110 to heat the fluid flowing therethrough.

In decision block 2115, the central controller 100 may determine if the pre-cool temperature assigned for the cryogenic chamber 200 has been achieved/met. The central controller 100 may be reading the two or more chamber sensors 105B in this decision block.

If the inquiry to decision block 2115 is negative, meaning the pre-cool temperature has not been achieved yet within chamber 200, then the "No" branch is followed back to block 2110. If the inquiry to decision block 2115 is positive, meaning the pre-cool temperature has been achieved/met within chamber 200, then the "Yes" branch is followed to block 2120.

In block 2120, the central controller 100 may generate one or more messages to indicate that the pre-cool temperature within the chamber 200 has been achieved. The central controller 100 may send messages to the display device 147 and/or the audio device 145 (see FIG. 1D). The audio device 145 may generate audible tones and/or synthesized/machine generated speech to indicate the pre-cool temperature within the chamber 200 has been achieved.

Next, in block 2125, the central controller 100 may display the cryotherapy session level/magnitude that was selected in block 2105 and it may allow the operator to select a different level/magnitude at this stage. Alternatively, if only the pre-cool stage was selected in block 2105 without any session level/magnitude, then this block 2125 may allow the operator to select a cryotherapy session level at this point as illustrated in FIG. 18.

Subsequently, after receiving the selected cryotherapy session level (i.e.—such as Level 1, Level 2, or Level 3) in block 2130, the central controller 100 may initiate the cryogenic therapy session by issuing commands to the remote controlled valve 120A for controlling cryogenic gas flowing through the primary spray head/nozzle 802. During this stage/block 2130, the central controller may monitor all temperature sensors 105 and issue commands automatically to the cryo-heater 110 as appropriate based on the temperature readings.

In decision block 2135, the central controller 100 may determine if a stop command has been issued by an operator. In this decision block 2135, the central controller may be monitoring an input device for this stop command. For example, the central controller 100 may be monitoring the touch-screen display device 147 such as illustrated in FIGS. 18 and 20 for any activation of the on-screen stop button 1808. The stop command may originate from other input devices, such as the mechanical emergency shut-off switch 505, being monitored by the central controller 100 but are not shown.

If the inquiry to decision block 2135 is positive, then the "Yes" branch is followed to block 2155 in which the cryotherapy session is stopped. If the inquiry to decision block 2135 is negative, meaning that the cryotherapy session should continue, then the "No" branch is followed to decision block 2140.

In decision block 2140, the central controller 2140 may determine if the operator of the system 101 has "checked-in" as part of a safety feature of the system 101. Decision block 2140 may correspond with screen display 1900 of FIG. 19. Screen display 1900 as described above illustrates an on-screen button 1905 which must be selected by an operator after a pre-determined time period for the cryotherapy session to continue. In this way, the system 101 needs an affirmation from the human operator that the human subject 10 within chamber 200 during a cryotherapy session is in a healthy state. Other and additional check-in features may be provided by the central controller 100.

As noted previously, in portable computing device context, this check-in feature may be sent to the portable computing device that is within a predetermined radius relative to the chamber 200. Alternatively, or additionally, the check-in feature may comprise a voice-command issued by the human operator in which the central controller 100 may be programmed to listen for a specific voice signature and particular command to continue a cryotherapy session.

If the inquiry to decision block 2140 is positive, then the "Yes" branch is followed to decision block 2150. If the inquiry to decision block 2140 is negative, meaning that the check-in command has not been received by the central controller 100, then the "No" branch is followed to decision block 2145.

In decision block 2145, the central controller 100 may determine if a predetermined amount of time has expired before the human operator has checked-in using the on-screen button 1905 of FIG. 19 (or some other or additional check-in feature described above). This predetermined amount of time may comprise a configuration setting that is set by the human operator as an initial setting. Alternatively or additionally, this predetermined amount of time may be a default setting. The predetermined amount of time may be set as a magnitude that is between about 10.0 seconds to about 30.0 seconds.

If the inquiry to decision block 2145 is positive, then the "Yes" branch is followed to block 2155 in which the cryotherapy session is stopped. If the inquiry to decision block 2135 is negative, meaning that the time limit has not be reached, then the "No" branch is followed to decision block 2140.

In decision block 2150, the central controller 100 may determine if the session time limit has been reached. As noted previously, in the exemplary embodiments illustrated, such as illustrated in FIG. 18A, at least three cryotherapy session levels, each with its own distinct time limit/duration may be provided. This is the time limit/duration that is checked in this decision block 2150 by the central controller 100. As noted previously, fewer or additional cryotherapy session levels may be provided and are within the scope of this disclosure as understood by one of ordinary skill in the art.

If the inquiry to decision block 2150 is positive, then the "Yes" branch is followed to block 2155 in which the cryotherapy session is stopped. If the inquiry to decision block 2150 is negative, meaning that the time limit has not be reached, then the "No" branch is followed back to decision block 2151.

In decision block 2151, the central controller 100 may determine if the cooling rate 1707 selected/set in FIG. 17B is being met. If the detected present cooling rate is greater than the selected threshold/set cooling rate 1707 of FIG. 17B [meaning the inquiry to decision block 2151 is negative, the "NO" branch is followed and], the central controller 100 may send commands in block 2154 to the heater controller 109 so that the heater 110 is turned "ON" to raise the temperature for the cooling rate. If the detected present cooling rate is less than a selected threshold/cooling rate 1707 of FIG. 17B [meaning the inquiry to decision block 2151 is negative, the "NO" branch is followed and], then the central controller 100 may send commands in block 2154 to the heater controller 109 so that the heater 110 is turned "OFF" to lower the temperature for the cooling rate.

If the detected present cooling rate is satisfactory or approximately equal to the cooling rate 1707 of FIG. 17B [meaning the inquiry to decision block 2151 is positive, the "YES" branch is followed and], the method continues to decision block 2152.

In decision block 2152, the central controller 100 may check-in with the heater controller 109 to determine if the heater 110 is in an overheat condition. If the heater controller 109 determines in decision block 2152 that the heater 110 is over heated, then the heater controller 109 in block 2152 sends this status to the central controller 100 and the "YES" branch is followed to block 2155.

If the inquiry to decision block 2152 is negative, meaning that the heater 110 is operating normally, then the "NO" branch is followed to decision block 2153. In decision block 2153, the central controller 100 may determine via pressure sensors/detectors 103 if the pressure within the plumbing 810 is under and/or over its predetermined range. As noted previously, according to one exemplary embodiment, the "normal range" for the plumbing 810 may comprise a range between about 18.0 pisg to about 30.0 psig. However, other ranges are possible and are included within the scope of this disclosure as understood by one of ordinary skill in the art.

If the inquiry to decision block 2153 is negative, meaning that the pressure is within the "normal range" for the plumbing 810, then the "NO" branch is followed back up to decision block 2140. If the inquiry to decision block 2153 is positive, meaning that the pressure is outside the "normal range" for the plumbing 810, then the "YES" branch is followed to block 2155.

In block 2155, the central controller 100 may issue commands to the one or more remote control valves 120 in order to close them which stops the cryotherapy session. In this block 2155, the central controller 100 may activate an audible and/or visual alarm if the cryotherapy session was stopped due to an emergency condition (i.e.—emergency stop signal received and/or check-in signal was not received, etc.). The central controller 100 may also display a message on the display device 147 corresponding to the alarm condition. If the cryotherapy session was stopped due to its natural expiration of its predetermined time limit, then the central controller 100 may issue audio signals to the audio device 145 and/or visual messages to the display device 147 as appropriate (i.e.—a bell sound/"ding"/chime to indicate a finished condition/sate and/or send a "session complete" message to the display device 147).

If the central controller 100 stopped a cyrotherapy session due to an overheat condition detected in decision block 2152, then in block 2155 the central controller 100 may generate the overheat message 1803F of FIG. 18E and/or the central controller may activate an audible alarm using the audio device 145.

Similarly, if the central controller 100 stopped a cyrotherapy session due to an out-of-pressure range condition detected in decision block 2153, then in block 2155 the central controller 100 may generate the out-of-pressure range message 1803C of FIG. 18D and/or the central controller may activate an audible alarm using the audio device 145.

Next, in block 2160, the central controller 100 may increment a counter to track the number of cryotherapy sessions that have been produced by the system 101. This counter may be useful for diagnostics information and for servicing the system 101. In block 2160, the central controller 100 may also store various statistics that may track the efficiency of the system 101. For example, the central controller 100 may track how many times and how much energy was expended with the heater 110 for each cryotherapy session. Additionally, the central controller 100 may determine how many times and how much energy was used for activating each remote controlled valve 120 as well as for monitoring the temperature sensors 105.

In decision block 2165, the central controller 100 may determine if a new cryotherapy session has been selected with the touch-screen display device 147. If the inquiry to decision block 2165 is positive, then the "Yes" branch is followed to block 2170 in which the central controller 100 assesses the need for any pre-cooling of chamber 200. If the inquiry to decision block 2165 is negative, meaning that a cryotherapy session has not been selected, then the "No" branch is followed so that the process returns back to block 2105.

In block 2170, the central controller 100 determines the difference between the pre-cool temperature setting, the current temperature of the chamber 200, and the selected cryotherapy session. Next, in decision block 2175, the central controller 100 determines if a pre-cool session is needed based on the parameters reviewed in block 2170. If the inquiry to decision block 2175 is negative, meaning that a pre-cool session is not needed, then the "No" branch is followed so that the process returns back to block 2125. If the inquiry to decision block 2175 is positive, then the "Yes" branch is followed to block 2110 in which the central controller 100 initiates a pre-cooling session of the cryogenic chamber 200.

Referring now to FIG. 22, this figure is a functional block diagram of an internet connected computer 100 that may embody/form the electronic central controller 100. The exemplary operating environment for the system 101 that comprises the CryoSauna/cryogenic chamber 200 includes a general-purpose computing device in the form of a conventional computer 100.

Generally, a computer 100 may include a processing unit 2221, a system memory 2222, and a system bus 2223 that couples various system components including the system memory 2222 to the processing unit 2221. The system bus 2223 may be any of several types of bus structures including a memory bus or memory controller, a peripheral bus, and a local bus using any of a variety of bus architectures. The system memory includes a read-only memory (ROM) 2224 and a random access memory (RAM) 2225. A basic input/output system (BIOS) 2226, containing the basic routines that help to transfer information between elements within computer 100, such as during start-up, is stored in ROM 2224.

The computer 100 can include a hard disk drive 2227A for reading from and writing to a hard disk, not shown, a supplemental storage drive for reading from or writing to a removable supplemental storage 2229 (like flash memory and/or a USB drive) and an optical disk drive 2230 for reading from or writing to a removable optical disk 2231 such as a CD-ROM or other optical media. Hard disk drive 2227A, magnetic disk drive 2228, and optical disk drive 2230 are connected to system bus 2223 by a hard disk drive interface 2232, a supplemental storage drive interface 2233, and an optical disk drive interface 2234, respectively.

Although the exemplary environment described herein employs hard disk 2227A, removable magnetic disk 2229, and removable optical disk 2231, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment without departing from the scope of the invention. Such uses of other forms of computer readable media besides the hardware illustrated will be used in internet connected devices.

The drives and their associated computer readable media illustrated in FIG. 4 provide nonvolatile storage of computer-executable instructions, data structures, program modules, and other data for computer or client device 100A. A number of program modules may be stored on hard disk 2227, magnetic disk 2229, optical disk 2231, ROM 2224, or RAM 2225, including, but not limited to, an operating system 2235, a temperature monitoring module 105, a valve control module 120, a heater control module 110, and a safety-check module 1905 that generates screen display 1900 of FIG. 19. The modules 105, 110, 120, and 1905 are described above in connection with FIG. 1D and FIG. 19.

Program modules include routines, sub-routines, programs, objects, components, data structures, etc., which perform particular tasks or implement particular abstract data types. Aspects of the present invention may be implemented in the form of software that provides for control of a cryotherapy chamber or cabin 200 illustrated above.

A user may enter commands and information into computer 100 through input devices, such as a keyboard 2240 and a pointing device 2242. As understood by one of ordinary skill in the art, the keyboard 2240 may be formed as part of or integral with a touch screen display 147, such as illustrated in FIG. 1D described above.

Pointing devices may include a mouse, a trackball, and an electronic pen that can be used in conjunction with an electronic tablet. Other input devices (not shown) may include a microphone, joystick, game pad, satellite dish, scanner, or the like. These and other input devices are often connected to processing unit 2221 through a serial port interface 2246 that is coupled to the system bus 2223, but may be connected by other interfaces, such as a parallel port, game port, a universal serial bus (USB), or the like.

The display 147 (such as illustrated in FIG. 1D, and FIGS. 17-20) may also be connected to system bus 2223 via an interface, such as a video adapter 2248. As noted above, the display 147 can comprise any type of display devices such as a liquid crystal display (LCD), a plasma display, an organic light-emitting diode (OLED) display, and a cathode ray tube (CRT) display.

The camera 2275 may also be connected to system bus 2223 via an interface, such as an adapter 2270. As noted previously, the camera 2275 can comprise a video camera such as a webcam. The camera 2275 can be a CCD (charge-coupled device) camera or a CMOS (complementary metal-oxide-semiconductor) camera. In addition to the monitor 2247 and camera 2275, the client device 100A, comprising a computer, may include other peripheral output devices (not shown), such as speakers and printers.

The computer 100 may operate in a networked environment using logical connections to one or more remote computers, such as the web server 100C of FIG. 22. A remote computer may be another personal computer, a server 100C, a mobile phone, a router, a network PC, a peer device, or other common network node. While the web server 100C or a remote computer typically includes many or all of the elements described above relative to the computer 1000, only a memory storage device 2227E has been illustrated in FIG. 22.

The logical connections depicted in FIG. 22 include a local area network (LAN) 2215A and a wide area network (WAN) 2215B. Such networking environments are commonplace in offices, enterprise-wide computer networks, intranets, and the Internet.

When used in a LAN networking environment, the computer 100 is often connected to the local area network 2215A through a network interface or adapter 2253. When used in a WAN networking environment, the computer 100 typically includes a modem 2254 or other means for establishing communications over WAN 2215B, such as the Internet. Modem 2254, which may be internal or external, is connected to system bus 2223 via serial port interface 2246. In a networked environment, program modules depicted relative to the server 100C, or portions thereof, may be stored in the remote memory storage device 2227E. It will be appreciated that the network connections shown are exemplary and other means of establishing a communications link between the computers 100 may be used.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the drawings, which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk and blu-ray disc where disks usually reproduce data magnetically, while discs reproduce data optically with lasers. Combinations of the above should also be included within the scope of computer-readable media.

Although a few embodiments have been described in detail above, those skilled in the art will readily appreciate that many modifications are possible in the embodiments without materially departing from this disclosure. Accordingly, such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, sixth paragraph for any limitations of any of the claims herein, except for those in which the claim expressly uses the words 'means for' together with an associated function.

Therefore, although selected aspects have been illustrated and described in detail, it will be understood that various substitutions and alterations may be made therein without departing from the spirit and scope of the present invention, as defined by the following claims.

What is claimed is:

1. A method for automatically producing and monitoring a cryotherapy session within a chamber comprising:
    receiving input for a first temperature for the chamber associated with the cryotherapy session within the chamber;

initiating a pre-cooling session for cooling the chamber to a second temperature which is different than the first temperature, the pre-cooling session comprising automatically activating a first remote control valve and a second remote control valve such that cryogenic gas flows into the chamber, and automatically activating a cryogenic heater when needed to keep the cryogenic gas at a predetermined temperature as the cryogenic gas exits a first nozzle and a second nozzle positioned within the chamber;

determining if the second temperature has been reached in the chamber;

deactivating the first and second remote control valves in response to determining that the second temperature has been reached in the chamber;

initiating the cryotherapy session within the chamber with the cryogenic gas for cooling the chamber to the first temperature, the cryotherapy session comprising automatically activating the second remote control valve, and automatically activating the cryogenic heater when needed to keep the cryogenic gas at a predetermined temperature as the cryogenic gas exits a third nozzle positioned within the chamber;

determining if the first temperature has been reached within the chamber;

determining if a cooling rate for the chamber is being met; and determining if an overheat condition for the cryogenic heater exists during the pre-cooling session and the cryotherapy session.

2. The method of claim 1, further comprising determining if a pressure for a cryogenic fluid that transforms into the cryogenic gas is within a predetermined range.

3. The method of claim 1, further comprising:
   determining if a stop command has been received for the cryotherapy session; and
   determining if a check-in command has been received for the cryotherapy session.

4. The method of claim 1, wherein receiving input for the first temperature comprises receiving input through a touch-screen display device.

5. The method of claim 1, further comprising determining if a predetermined time limit associated with the cryotherapy session has expired.

6. The method of claim 5, wherein if the predetermined time limit associated with the cryotherapy session has expired, then stopping the cryotherapy session.

7. The method of claim 3, further comprising determining if a predetermined time limit associated with the check-in command has expired.

8. The method of claim 5, wherein if a predetermined time limit associated with the check-in command has expired, then stopping the cryotherapy session.

9. The method of claim 1, further comprising displaying a plurality of different cryotherapy sessions that are selectable.

10. A system for automatically producing and monitoring a cryotherapy session within a chamber comprising:

means for receiving input for a first temperature for the chamber associated with the cryotherapy session within the chamber;

means for initiating a pre-cooling session for cooling the chamber to a second temperature which is different than the first temperature, the pre-cooling session comprising the means for initiating the pre-cooling session automatically activating a first remote control valve and a second remote control valve such that cryogenic gas flows into the chamber, and the means for initiating the pre-cooling session automatically activating a cryogenic heater when needed to keep the cryogenic gas at a predetermined temperature as the cryogenic gas exits a first nozzle and a second nozzle positioned within the chamber;

means for determining if the second temperature has been reached in the chamber;

means for deactivating the cryogenic heater and the first and second remote control valves in response to determining that the second temperature has been reached in the chamber;

means for initiating the cryotherapy session within the chamber with the cryogenic gas for cooling the chamber to the first temperature, the cryotherapy session comprising the means for initiating the cryotherapy session automatically activating the second remote control valve, and the means for initiating the cyrotherapy session automatically activating a cryogenic heater when needed to keep the cryogenic gas at a predetermined temperature as the cryogenic gas exits a third nozzle positioned within the chamber;

means for determining if the first temperature has been reached within the chamber;

means for determining if a cooling rate for the chamber is being met; and means for determining if an overheat condition for the cryogenic heater exists during the pre-cooling session and the cryotherapy session.

11. The system of claim 10, further comprising:
    means for determining if a stop command has been received for the cryotherapy session; and
    means for determining if a check-in command has been received for the cryotherapy session.

12. The system of claim 10, wherein the means for receiving input for the first temperature comprises a touch-screen display device.

13. The system of claim 10, further comprising means for determining if a predetermined time limit associated with the cryotherapy session has expired.

14. The system of claim 13, further comprising means for stopping the cryotherapy session when the predetermined time limit associated with the cryotherapy session has expired.

15. The system of claim 11, further comprising means for determining if a predetermined time limit associated with the check-in command has expired.

16. The system of claim 15, further comprising means for stopping the cryotherapy session when a predetermined time limit associated with the check-in command has expired.

* * * * *